(12) United States Patent
Yamashita

(10) Patent No.: US 9,040,291 B2
(45) Date of Patent: May 26, 2015

(54) CONSTANT-TEMPERATURE EQUIPMENT

(75) Inventor: Seishi Yamashita, Fukuyama (JP)

(73) Assignee: Rorze Corporation, Hiroshima (JP)

( * ) Notice: Subject to any disclaimer, the term of this patent is extended or adjusted under 35 U.S.C. 154(b) by 658 days.

(21) Appl. No.: 12/737,332

(22) PCT Filed: Jun. 30, 2009

(86) PCT No.: PCT/JP2009/061902
§ 371 (c)(1),
(2), (4) Date: Dec. 30, 2010

(87) PCT Pub. No.: WO2010/001874
PCT Pub. Date: Jan. 7, 2010

(65) Prior Publication Data
US 2011/0097787 A1    Apr. 28, 2011

(30) Foreign Application Priority Data
Jul. 1, 2008  (JP) ................... 2008-172491

(51) Int. Cl.
*C12M 1/00*     (2006.01)
*C12M 3/00*     (2006.01)
*B01L 1/02*     (2006.01)
*G01N 35/00*    (2006.01)
*G01N 35/04*    (2006.01)

(52) U.S. Cl.
CPC ............. *C12M 41/14* (2013.01); *B01L 1/025* (2013.01); *G01N 2035/00356* (2013.01); *G01N 2035/0425* (2013.01)

(58) Field of Classification Search
CPC ............ G01N 35/042; G01N 35/0462; G01N 35/0465; G01N 35/0099; G01N 35/02; G01N 35/028

USPC .................... 435/283.1, 303.1–303.3, 809
See application file for complete search history.

(56) References Cited

U.S. PATENT DOCUMENTS

| | | | |
|---|---|---|---|
| 6,228,636 B1 * | 5/2001 | Yahiro et al. | 435/303.1 |
| 2003/0031602 A1 | 2/2003 | Weselak et al. | |
| 2004/0152188 A1 * | 8/2004 | Yamamoto et al. | 435/287.3 |
| 2007/0041814 A1 * | 2/2007 | Lowe | 414/273 |
| 2007/0107739 A1 | 5/2007 | Sato et al. | |
| 2007/0281351 A1 | 12/2007 | Kobayashi et al. | |

FOREIGN PATENT DOCUMENTS

| | | |
|---|---|---|
| JP | 61-182300 | 11/1986 |
| JP | 05-088298 | 12/1993 |
| JP | 05-96564 | 12/1993 |

(Continued)

*Primary Examiner* — Michael Hobbs
(74) *Attorney, Agent, or Firm* — Merek, Blackmon & Voorhees, LLC

(57) ABSTRACT

Constant-temperature equipment wherein mechanical and electrical structures are eliminated from the inside of a temperature-controlled chamber (15) by using a non-contact magnetic arrangement as a drive transmission for a sample table (5) and a sample table drive mechanism (6), thus reducing failure and enhancing maintainability. In addition, a conveyance mechanism (11) is provided with a pass box adjacent which sliding shielding plates (9) are stacked vertically, and the shielding plates (9) are linked with the conveyance mechanism (11) by an engaging mechanism provided in the conveyance mechanism (11) to allow the plates to be opened and closed by a travel mechanism (12), thus simplifying the structure and minimizing change in atmosphere during conveying. The sample table drive mechanism (6) and the conveyance mechanism (11) can be attached removably to the temperature-controlled chamber (15) to permit sterilization at high temperature.

7 Claims, 17 Drawing Sheets

(56) References Cited

FOREIGN PATENT DOCUMENTS

| JP | 11-166555 | 6/1999 |
| JP | 2001-000172 | 9/2001 |
| JP | 2005-500522 A | 1/2005 |
| JP | 2007-132467 | 5/2007 |
| WO | WO 03/008103 | 1/2003 |

\* cited by examiner

CONSTANT-TEMPERATURE EQUIPMENT

CROSS-REFERENCE TO RELATED APPLICATION

The present application claims the priority under 35 U.S.C. 119 of Japanese Application No. 2008-172491, filed Jul. 1, 2008, which is hereby incorporated herein by reference in its entirety.

FIELD OF THE INVENTION

The invention relates to constant-temperature equipment for maintaining at least an even temperature.

BACKGROUND OF THE INVENTION

Constant-temperature equipment has been made use of to culture or test microbes and cells and so on. The constant-temperature equipment is formed by providing it with means for maintaining environmental conditions such as temperature, humidity and density of carbon dioxide to a temperature-controlled chamber for containing many samples which are the subject of culturing and testing. Culturing and testing are carried out continuously for many hours, and during these processes, it is necessary to regularly determine the conditions of each sample. Therefore, it is indispensable to regularly take out the sample from the temperature-controlled chamber to examine and analyze it. Therefore, much of the constant-temperature equipment introduced recently is equipped with memory means, arithmetic means and a conveyance mechanism to automate its process. The equipment has a function for automatically carrying out moving a container with a sample out and in, delivering it to processes for examining and analyzing, and handling the sample conditions. According to this, culturing and testing for the long term can be efficiently carried out.

PRIOR ART

Patent Literature

Patent literature 1: Japanese Patent Laid Open Publication No. 2001-172
Patent literature 2: Japanese Patent Laid Open Publication No. 2005-500522

DISCLOSURE OF THE INVENTION

Problems to be Solved by the Invention

However, as for conventional constant-temperature equipment with an automatic conveying function, various problems are caused on carrying out culturing and testing because there are mechanical and electrical components in the temperature-controlled chamber. The conventional constant-temperature equipment is affected by environments, such as temperature and humidity, during culturing to cause a high frequency of trouble. Even if repair or maintenance is carried out, much time is required, and culturing and testing start late because the equipment structure is complicated. Furthermore, when trouble occurs in the middle of culturing or testing, the reliability of the culturing and testing may be greatly affected.

On the other hand, miscellaneous germs must be removed from the inside of the temperature-controlled chamber before starting culturing and testing. This is because new cells or microorganisms to be cultured and tested next are affected, and the reliability of culturing and testing for the long time may be harmed if miscellaneous germs in the air or cells and microorganisms previously used in culturing and testing are left in the temperature-controlled chamber. Accordingly, in the conventional incubator, sterilizing treatments such as ultraviolet sterilization or dry sterilization have been carried out, or sterilization has been carried out by wiping off with medical solution.

However, various problems occur on carrying out the above-mentioned sterilizing treatments with the conventional control-temperature equipment having the automatic conveying function. For example, in the ultraviolet sterilization, ultraviolet rays do not reach the shadow of a structure, and therefore, they must be applied from various directions many times. In the case of the dry sterilization, electric components and sealing members are damaged at high temperature from 150° C. to 180° C. Accordingly, the dry sterilization has been carried out at low temperature which does not damage the components, or the inside has been taken apart to wipe off with the medical solution.

In the case of constant-temperature equipment with a small opening only for an automatic conveyance to move the container in and out of the chamber, even if a door is provided to keep the inside of the chamber isolated from the outside, it must be opened when taking the container in and out. The atmosphere inside the temperature-controlled chamber is affected by the outside environment to decrease the reliability of culturing and testing. The culturing and testing are carried out over a long time, and therefore, a solution for the above-mentioned problems has been strongly hoped for.

An object of the invention is to effectively solve the above-mentioned problems.

Means to Solve the Problem

The constant-temperature equipment of the invention comprises a temperature-controlled chamber, a slide frame, a plurality of shielding plates and a conveyance mechanism. The temperature-controlled chamber has a sample shelf support having a plurality of shelves provided on the inside, and also has an opening portion which is open to the outside at the position of the shelves of the sample shelf support. The slide frame is provided along a side edge of the opening portion. The shielding plates are guided by the slide frame, closing the opening portion. Each shielding plate closes and opens an interval between adjoining shielding plates while being guided by the slide frame. The conveyance mechanism has detachable pieces which are attached removably to the shielding plates and moves on the shielding plates along the side edge of the opening portion.

The temperature-controlled chamber of this invention is a chamber for accommodating the sample, being a part of the constant-temperature equipment for regulating the gas density such as moisture, oxygen, nitrogen, carbon dioxide, besides keeping the inside temperature constant at least. Especially, the constant-temperature equipment of this invention is most suitable for a culture vessel to be used in biology.

Effects of the Invention

According to the above-mentioned structure, the conveyance mechanism can access the inside of the temperature-controlled chamber within the range of a pass box having a required capacity, and therefore, it is possible to maintain a stable culturing and testing environment without affecting an internal environment in which the temperature and the humidity are kept constant while a container is moved in and out.

According to the structure wherein the shielding plates are opened and closed by sliding and shielding plates except at a required opening portion are closed, it is possible to maintain a stable culturing and testing environment without any currents in the temperature-controlled chamber occurring at the time of opening and closing.

PREFERRED EMBODIMENT OF THE INVENTION

Figure 1:
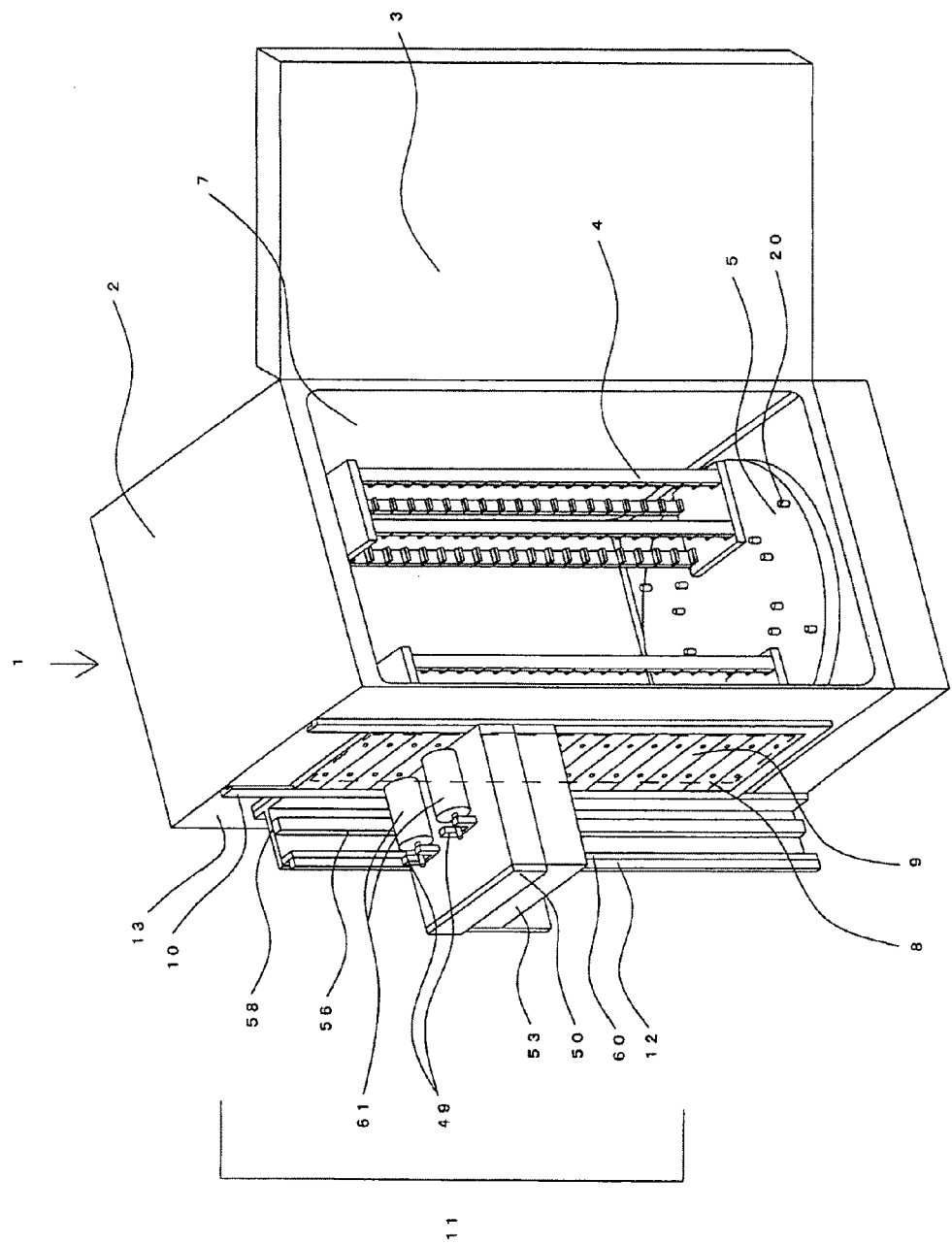
FIG. 1 is a perspective view of constant-temperature equipment of an embodiment of the invention.
Figure 2:
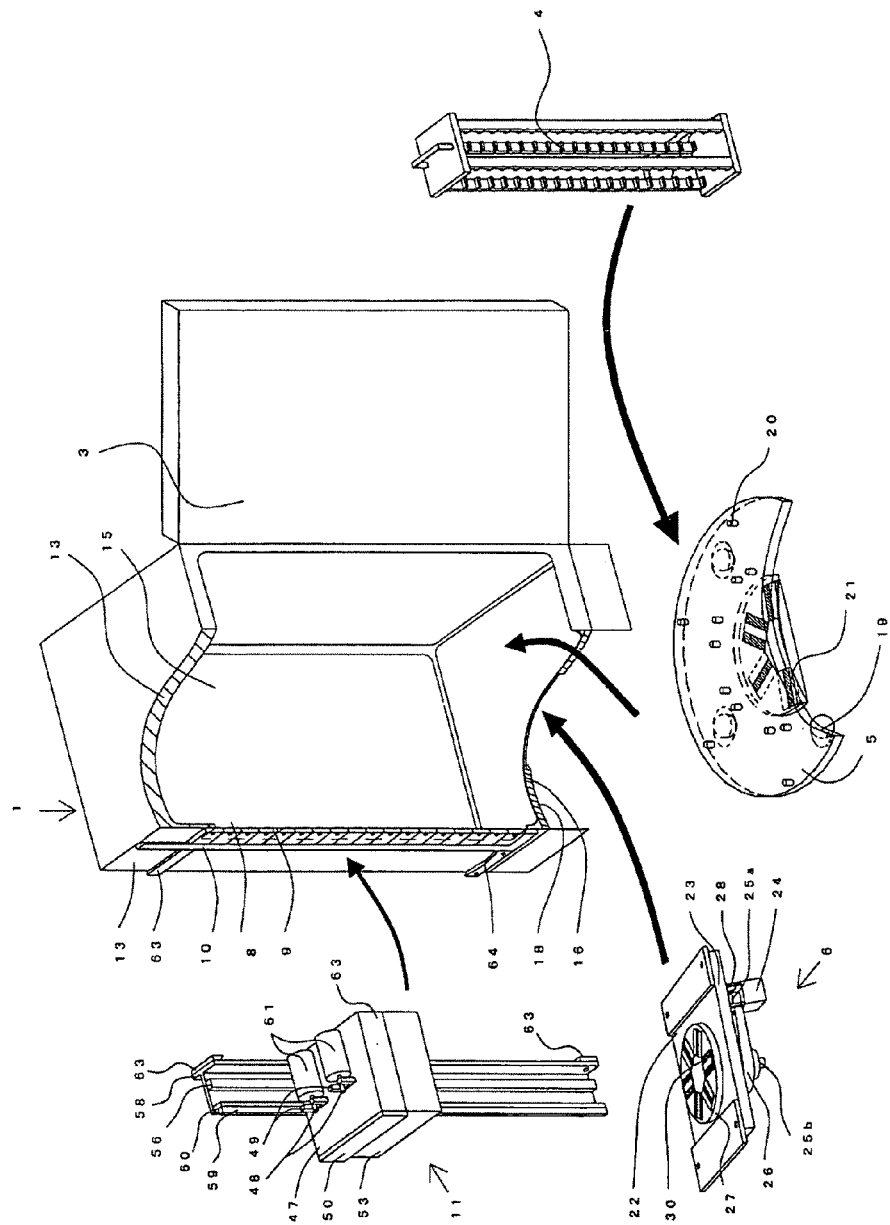
FIG. 2 is a view of a removable part of constant-temperature equipment of an embodiment of the invention.

An embodiment of the invention will be explained with reference to following drawings. FIG. 1 is a perspective view of constant-temperature equipment 1 of this embodiment, and FIG. 2 illustrates a state in which removable parts are separated from the constant-temperature equipment 1. The constant-temperature equipment 1 comprises a box 2, a door 3, a sample table 5 for placing a sample shelf support 4, and a sample table drive mechanism 6 for rotating the sample table 5. The box 2 has two openings. One is a large opening 7 for moving the sample shelf support 4 or the sample table 5 in and out, and for carrying out maintenance. The other is a small opening 8 for moving a sample container 14 loaded on each shelf of the sample shelf support 4 in and out. The small opening 8 forms a liner opening having a length for exposing all shelves of the sample shelf support 4 to the outside of the constant-temperature equipment 1. The large opening 7 has the door 3, which closes the large opening, provided on hinges so as to be freely opened and closed.

A plurality of shielding plates 9 are vertically arranged on one another across the small opening 8 in accordance with the number of shelves in the vertical direction of the sample shelf support 4 and are movable along a slide frame 10. Each shielding plate 9 has an area large enough to individually move a sample container 14 in and out. The slide frame 10 guides the shielding plates 9 in the vertical direction. Here, a temperature-controlled chamber 15 forms a space isolated from the outside by shielding the small opening 8 with the shielding plates 9.

Conveyance mechanism 11, which moves the sample container 14 in and out, is attached removably at a position facing the shielding plates 9. In addition, a travel mechanism 12, which is a part of the conveyance mechanism 11, moves up and down the conveyance mechanism. According to this, by combining various workings of a drive mechanism provided on the conveyance mechanism 11, it is possible to open and close the shielding plates 9, and to hold up, carry in and out and place the sample container 14. Furthermore, the conveyance mechanism 11 is attached removably on an external wall 13 of the constant-temperature equipment 1, and can be removed from the constant-temperature equipment 1.

Means for keeping the environment in the temperature-controlled chamber 15 at required conditions, which is not illustrated in drawings, is provided in a space 17 formed by an internal wall 16 of the temperature-controlled chamber 15 and the external wall 13. Environmental conditions such as the temperature inside the temperature-controlled chamber 15 and the density of carbon dioxide therein are kept as required.

Figure 3:
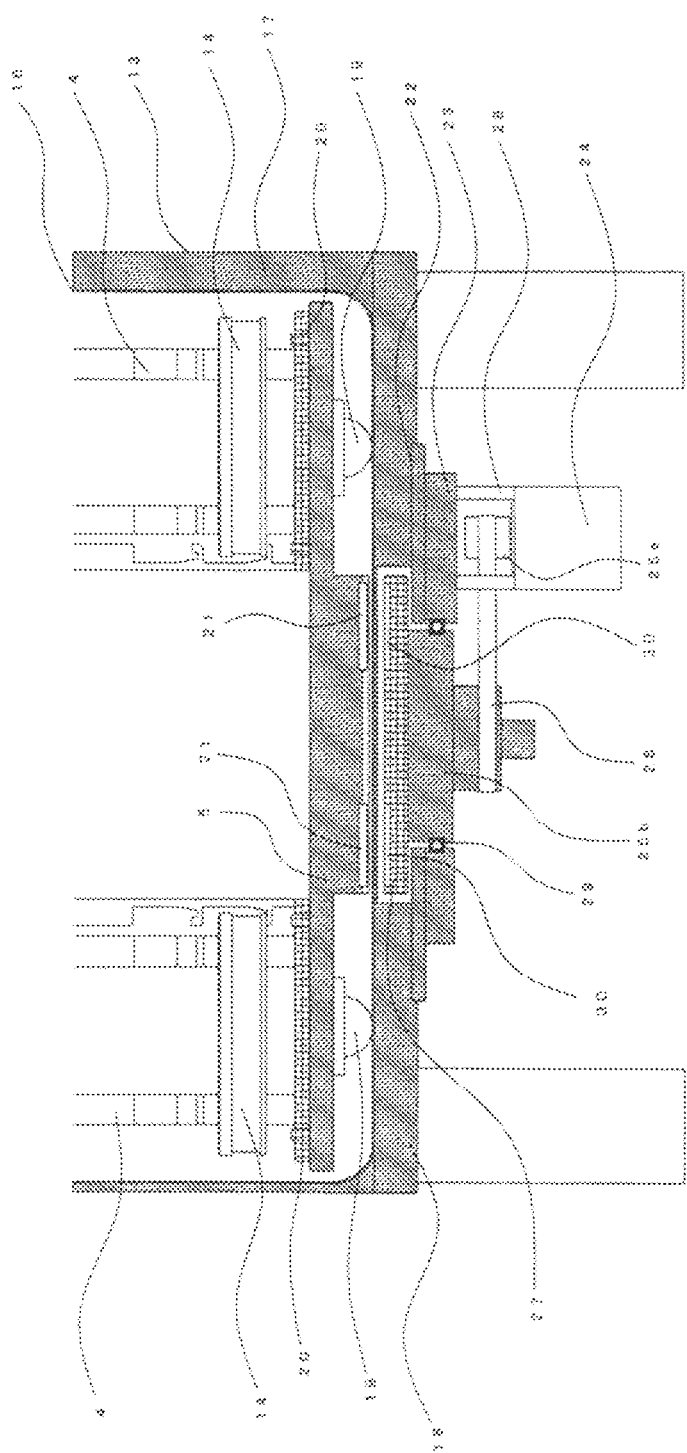
FIG. 3 is a sectional view of constant-temperature equipment of an embodiment of the invention.

Next, the internal structure of the box 2 and the sample table drive mechanism 6 will be explained with reference to FIG. 2 and FIG. 3. The internal wall 16 and the external wall 13 are fixed on a baseboard 18. The internal wall 16 completely encloses the temperature-controlled chamber 15, except for the large opening 7 and the small opening 8. The temperature-controlled chamber 15 contains the sample container 14 including a sample, the sample shelf support 4 for holding a plurality of sample containers 14, and the sample table 5 for placing a plurality of sample shelf supports 4.

The sample table 5 has rolling bodies 19, such as ball casters, fitted on the back side of the bottom at regular intervals so as to be installed movably on the floor inside the temperature-controlled chamber 15. In addition, the sample table 5 has driven magnets 21 fixedly placed on the back side so as to follow the working of driving magnets 30, which are provided on the sample table drive mechanism 6 as a magnetic generator. Although the illustrated embodiment has the rolling bodies 19, even in another example wherein an assembly made with materials having low frictional resistance instead of rolling members is fitted on the bottom, the same effects can be obtained. Moreover, the sample table 5 has a locational tool 20 provided on the top, enabling positioning of the sample shelf support 4.

Figure 13:
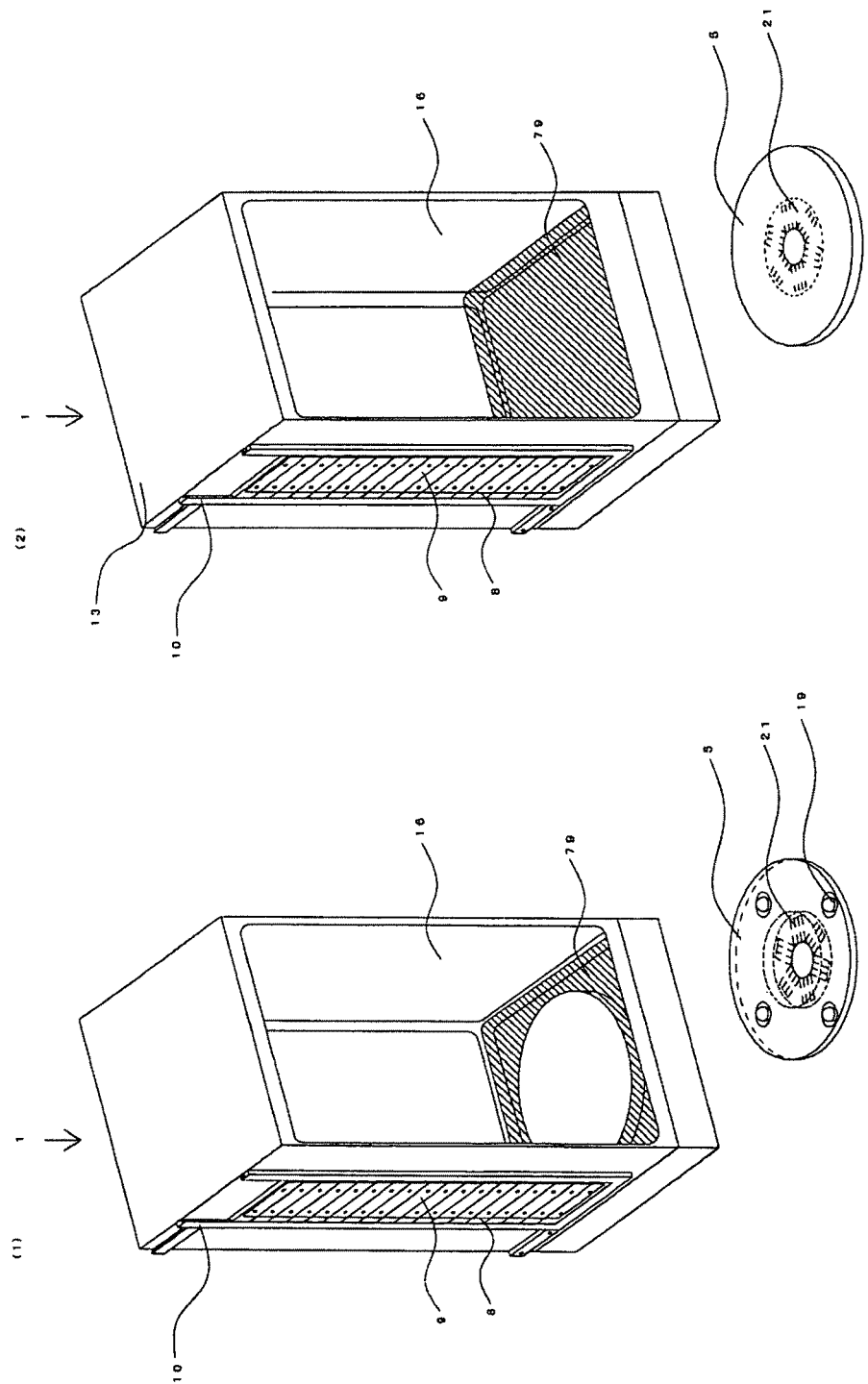
FIGS. 13(1)-13(2) are views showing water saving portions on floors of temperature-controlled chambers.

In examples shown in FIGS. 13(1) and 13(2), a water saving portion 79 for maintaining humidity is provided therein. In FIG. 13(1), a cavity for saving demineralized water is formed by lowering the floor on which the rolling bodies 19 are mounted. In addition, the temperature-controlled chamber 15 saves demineralized water throughout the bottom. In the example of FIG. 13(2), the temperature-controlled chamber 15 maintains humidity by filling the bottom with the demineralized water. In this case, water resistance is improved by using rolling bodies 19 made of resin or by covering all of the bottom of the sample table 5 with low frictional resistance members.

The sample table drive mechanism 6, which drives the sample shelf support 4 in either direction and at a variable speed, is installed on the back side of the bottom of the baseboard 18 through a heat insulating material 22. According to this, even if the inside of the temperature-controlled chamber 15 is kept at a high temperature, components of the sample table drive mechanism 6 are hardly affected by the heat in the temperature-controlled chamber 15. The sample table drive mechanism 6 comprises a driving housing unit 23 like a plate, a gear motor 24, pulleys 25a and 25b, a belt 26 and a magnet housing 27. The gear motor 24 is installed on the housing unit 23 through a spacer 28. The sample table drive 6 has all of its components implemented on the housing unit 23, the sample table drive being attached removably to the temperature-controlled chamber 15 as one body by fitting the housing unit 23 to the outside of the baseboard 18 with screws. The housing unit 23 can be also fixed with bolts. If thumbscrews are used, it is possible to easily carry out maintenance.

The gear motor 24 is electrically connected to a not-illustrated control assembly to set up parameters of the operation of the equipment by an input, such as a keyboard. The pulley 25a is fixed to the shaft of the gear motor 24. The rotary force of the gear motor 24 is transmitted to the pulley 25b by the belt 26. Here, the pulley 25b is rotatively assembled on the housing unit 23 through bearings 29.

The pulley 25b is fixed to the magnet housing 27 on which a plurality of driving magnets 30 is installed. Rotations of the motor are transmitted to the magnet housing 27 at a fixed speed ratio through the pulleys 25a and 25b and the belt 26. In addition, the driving magnets 30 are fixed with respect to the magnetic poles of the driven magnets 21 fixed on the bottom of the sample table 5 such that they pull against each other. According to this, the movements of the magnet housing 27 are transmitted to the sample table 5 through the magnetic force to operate the sample table 5. In this case, the baseboard 18 and the walls of the temperature-controlled chamber 15A are formed by materials having no magnetism or poor magnetism. In addition, according to this structure, when the sample table 5 is brought out from the temperature-controlled chamber 15 to the outside, it can be brought out by merely picking it up with one hand, without tools.

There is no structure on the bottom of the temperature-controlled chamber 15. Furthermore, no positioning member is provided. Therefore, positioning the sample table 5 becomes a problem. However, the sample table 5 can be located at almost the same position it had before removal, because of the mutual magnetic forces of the magnets arranged on the magnet housing 27 of the sample table 5 and the sample table drive mechanism 6. Besides, a self-aligning action takes place because the sample table 5 rotates by following the rotary movements of the magnet housing 27. That is, the sample table 5 can be reinstalled with great positional repeatability by placing its rotational center axis on the rotational center axis of the magnet housing 27.

The sample table drive 6 uses a stepping motor or a servo motor as a driving force. Accordingly, when the electric current is cut off, or the gear motor 24 loses synchronism, positional data have disappeared occasionally. Therefore, in this case, the position must be confirmed once more. The control assembly can determine the position of the sample table 5 by providing means for detecting positions on the outside of the temperature-controlled chamber 15 and a detected substance on the sample table 5 as means for confirming positions.

Figure 9:
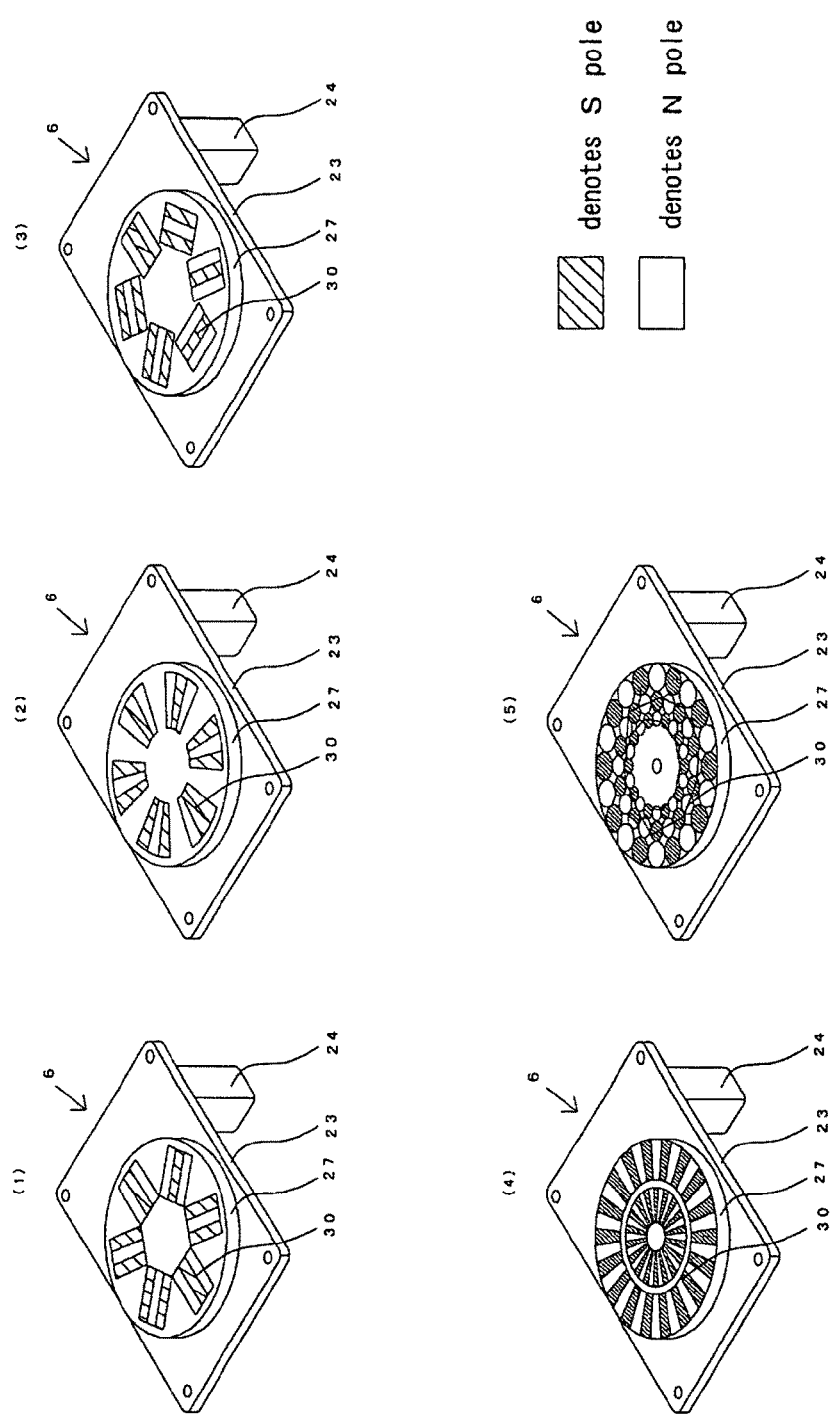
FIGS. 9(1)-9(5) are views showing various arrangements magnets sample table drive mechanism.
Figure 10:
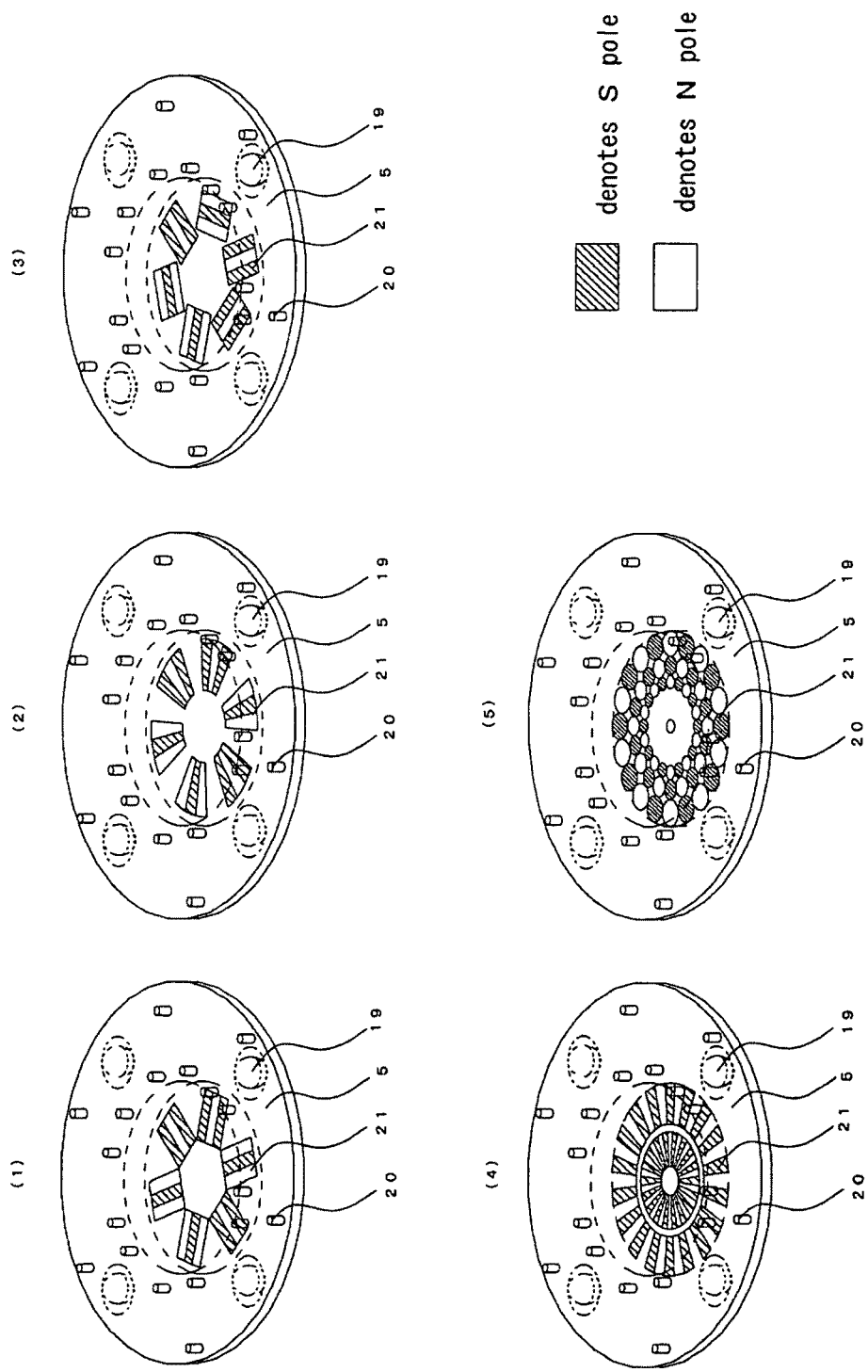
FIGS. 10(1)-10(5) are views showing various forms of magnets arranged on a sample table.

Next, the driven magnets 21 and the driving magnets 30 will be explained. FIG. 9 is a perspective view of the sample table drive mechanism 6. FIG. 10 is a perspective view of the sample table 5, from the top of the sample table. The sample table drives 6 of FIGS. 9(1) to 9(5) and the respective sample tables 5 of FIGS. 10(1) to 10(5) form combinations for driving force transmission. In the example of FIGS. 9(1) and 10(1), rectangular magnets are used by combining magnets with alternately arranged N poles and S poles in sets of three magnets each. There are two kinds of sets, N-S-N and S-N-S. In the example, all of the magnets of the sample table 5 and the magnet housing 27 are arranged so as to pull against each other only when the sample table 5 rotates at a fixed angle with respect to the magnet housing 27.

According to this, even if the sample table 5 is removed from the temperature-controlled chamber 15 and reinstalled therein by hand, it can be replaced at the previous rotary position by rotating it therein and locating it at the rotary position having the strongest magnetic force.

In FIGS. 9(2) and 10(2), the magnets are in sets of three magnets each, the same as in FIGS. 9(1) and 10(1), except that each set in FIGS. 9(2) and 10(2) forms is shaped to define a sector of a circle whose center corresponds with the center of the magnet housing 27. In FIGS. 9(3) and 10(3), the magnets are in sets of three magnets each, the same as in FIGS. 9(1) and 10(1), except the sample table 5 is arranged so that the rotational center is close to the rotational center of the magnet housing 27 by extending the magnets of some sets in the rotational direction and extending the magnets of other sets in the radial direction. Due to this arrangement, power transmission in the rotational direction can be effectively obtained. That is, a self-aligning effect can be obtained more effectively.

In FIGS. 9(4) and 10(4), a stronger magnetic force can be obtained by installing magnets shaped as sectors of circles covering the whole magnet housing 27. In FIGS. 9(5) and 10(5), a stronger magnetic force can be obtained by installing large and small circular magnets covering the whole magnet housing 27. The magnets can be selected to have various forms, numbers, combinations and arrangements. However, it goes without saying that it is desirable that the driven magnets 21 of the back side of the sample table 5 and the driving magnets 30 of the top of the magnet housing 27 have a common form, number and arrangement and that the facing magnets have magnetic poles that pull against each other. Further, the driving magnet 30 has a stronger magnetic force by using a yoke.

Figure 4:
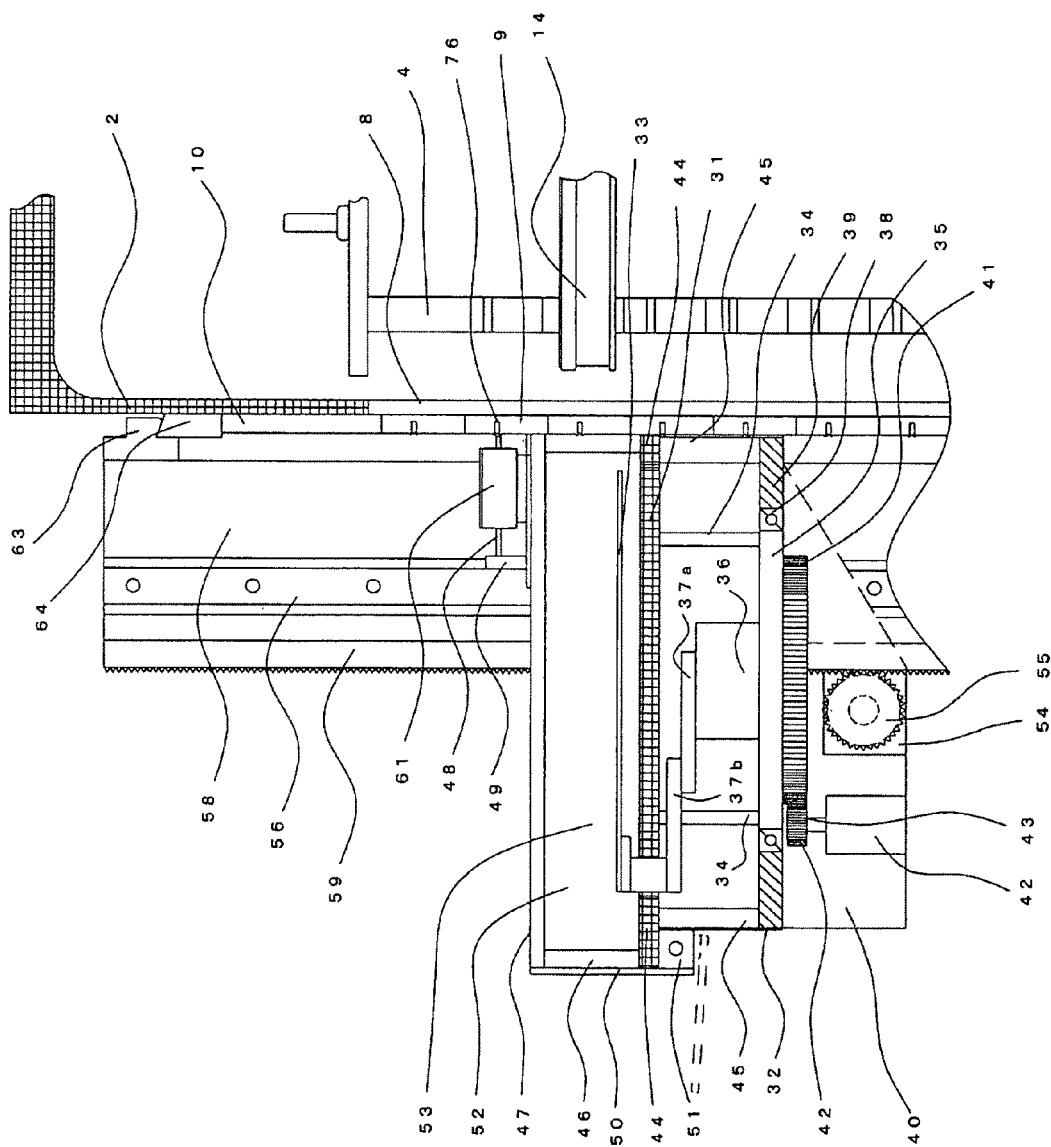
FIG. 4 is a sectional view showing an embodiment of a conveyance mechanism.

Next, the conveyance mechanism 11 will be explained with reference to FIG. 4. A gear motor 36 is fixed on a slewing table 35, and one end of a first arm 37a is installed on a rotational axis of the gear motor 36. The other end of the first arm 37a is connected to the base end of a second arm 37b, and the other end of the second arm 37b is connected to the base end of a finger 33. Here, the first arm 37a and the second arm 37b constitute an arm mechanism for advancing and retracting the finger 33. The rotary motions of the gear motor 36 are transmitted to advance and retract the finger 33 at a fixed speed ratio through the first arm 37a and the second arm 37b by installing them with a fixed speed ratio.

The slewing table 35 and a circular table 31 are fixed with spacers 34. The slewing table 35 is rotatively installed on a base shelf 39 through bearings 38 to form a slewing mechanism. The base shelf 39 is fixed on a plate 40. The slewing table 35 is provided with a gear 41 for engaging with a gear 43 fixed to the shaft of a slewing motor 42, which is fixed on the plate 40. According to this, the circular table 31 fixed on the slewing table 35, the gear motor 36, and the first arm 37a, the second arm 37b and the finger 33 fitted to the gear motor 36 are driven by the slewing motor 42.

A shield shelf 44, which is provided with an opening having a diameter larger than the circular table 31, is fixed on the base shelf 39 through a fixing block 45 so as to be opposite the circular table 31. Accordingly, the circular table 31 and the shield shelf 44 serve as a partition between a pass box 53 for passing through the sample container 14 and the outside having the drive.

The shield shelf 44 has a top plate 47 installed at its top through blocks 46. The top plate 47 has a detachable piece (an engaging pin 48 in the example) installed on its upper surface. The detachable piece is engaged in a recess is formed in the shielding plate 9, and is advanced and retracted by the electromagnetic force of a solenoid 61. The engaging pin 48 extends into the solenoid 61. The engaging pin 48 is advanced by the solenoid 61 to engage the shielding plate 9. The engaging pin 48 is retracted by the solenoid 61 to release the engagement. In addition, the engaging pin 48 has a sensor 49 provided at its rear to sense the position of the engaging pin for being advanced and retracted.

The shield shelf 44 has an opening/closing door 50 fitted behind the finger 33 so as to freely open and close. The opening/closing door 50 is opened and closed by a rotary source 51. Although a solenoid is used as the rotary source 51 in the present embodiment, a spring, an air-cylinder, or a motor can be used instead. The shield shelf 44 and the top plate 47 are opposite the shielding plate 9 in a slight opening, having side walls 52 to the left and right sides. Accordingly, when the small opening 8 is opened, the pass box 53 serves as a buffer room for reducing the change of the atmosphere in the temperature-controlled chamber 15. Here, the pass box 53 comprises the shielding plates 9, the top plate 47, the opening/closing door 50, the side walls 52, the slewing table 35, the base shelf 39 and the shield 32. To heighten the isolating property, each contact portion has a not-illustrated rubber sealing member provided.

Figure 11:
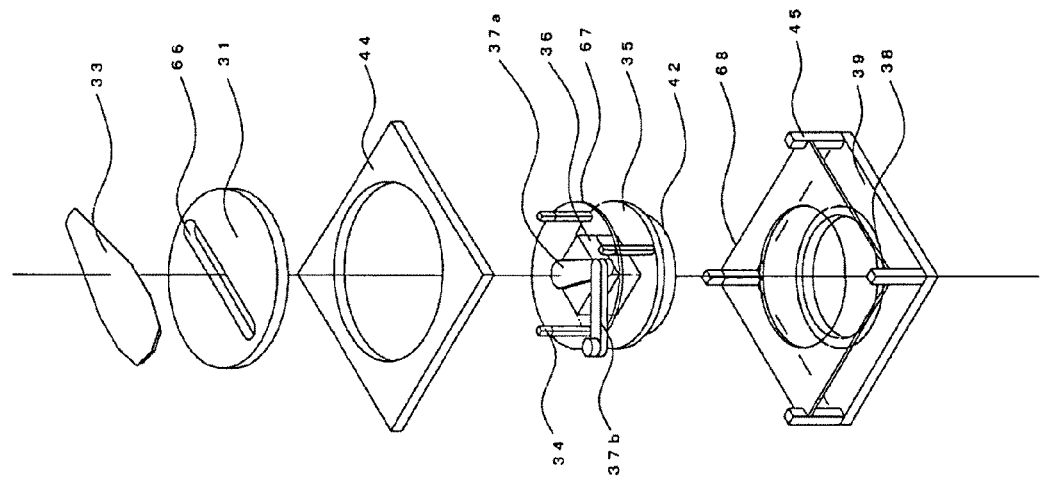
FIG. 11 is a view explaining an example of conveyance mechanism.
Figure 11:
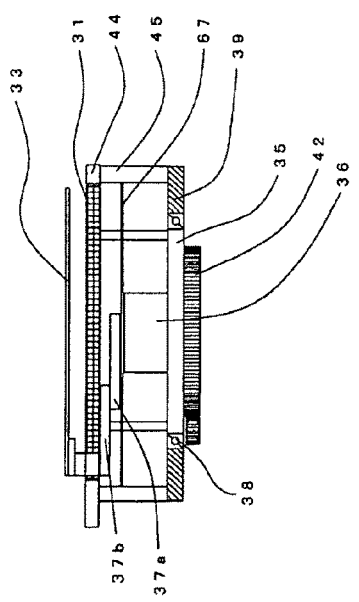

In the above-mentioned example, the circular table 31 has a slot 66 extending in the direction of movement of the finger 33 to operate a coupling portion of the second arm 37b and the finger 33. However, according to this, the atmosphere from the temperature-controlled chamber 15, having high temperature and high humidity, passes through the slot 66 when the shielding plates 9 are open. In this case, the motor 36 may be damaged. Therefore, as shown in FIG. 11 of the other example, the atmosphere can be prevented from entering the motor 36 by providing a slewing shielding plate 67 and a fixed shielding plate 38 between the motor 36 and the first arm 37a.

Figure 12:
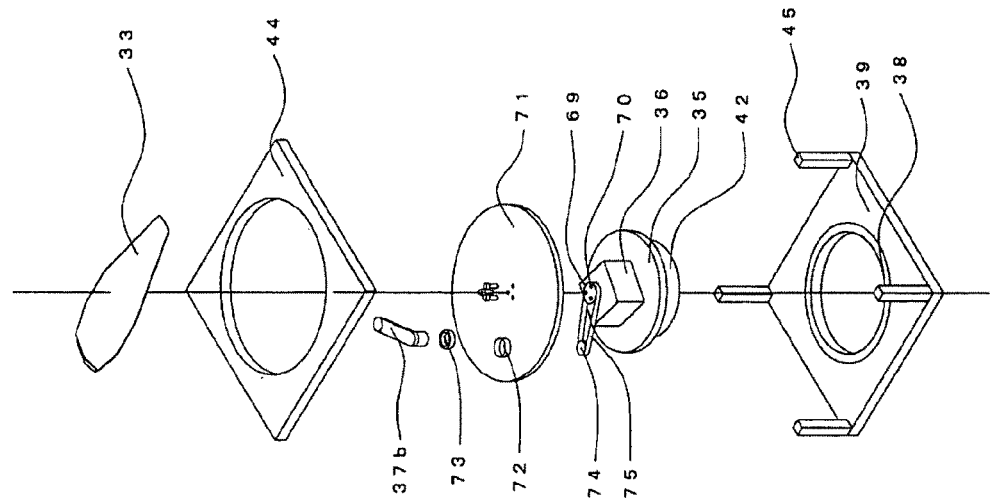
FIG. 12 is a view explaining another example of conveyance mechanism.
Figure 12:
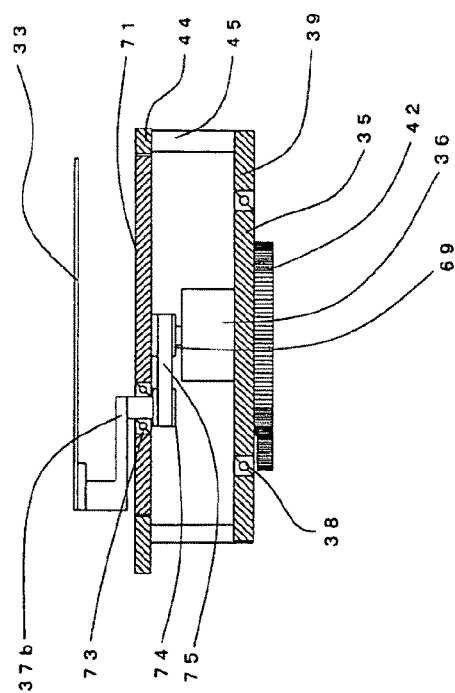

Furthermore, there is another example as shown in FIG. 12. Instead of the first arm 37a, a pulley 69 and a shielding plate 71 are concentrically fixed on the shaft of the motor 36. The shielding plate 71 has an extract hole 72 whose center is on the slewing track of the first arm 37a, and therein, the second arm 37b is inserted from the side of the finger 33 through a bearing 73. A pulley 75 is installed to connect the second arm 37b and the first arm 37a. When the rotary speed ratio of the pulley 69 and the pulley 74 is made the same as the first arm 37a, the pulley 69 and the shielding plate 71 are rotated by the motor 36. In addition, rotations of the pulley 69 are transmitted to the pulley 74 through a belt 75 to advance and retract the second arm 37b through the finger 33.

According to this method, the shield shelf 44 and the shielding plate 71 serve as a partition so that the mechanical structure below the second arm 37b can be isolated from the atmosphere having high temperature and high humidity in the temperature-controlled chamber 15. The isolating property is heightened by providing a bearing between the shielding plate 71 and the shield shelf 44.

Next, the travel mechanism 12, which is a part of the conveyance mechanism 11, will be explained with reference to FIGS. 4 and 5. The plate 40 has an elevator gear motor 54 for traveling installed, and the motor shaft has a pinion gear 55 fixed thereto. In addition, the plate 40 has a movable terminal 57 of a slide guide 56 fixed on the back side, moving along the track of the slide guide 56 installed on an elevator base 58. The slide guide 56 of the elevator base 58 has a rack gear 59 having teeth for engaging with the pinion gear 55 installed through a rack base 60.

The elevator base 58 and the rack base 60 are detachably installed on the box 2 through brackets 63, 64 so that plural engaging pins engage in engaging holes 76 of the opposite shielding plate 9. Therefore, the engaging pins 48 are reliably engaged with one of the shielding plates 9, which is located at any position from the lowermost shelf to the uppermost shelf. Needless to say, the slide guide 56 and the rack gear 59 have a stroke long enough to the shielding plates 9 up one step at any point from the lowermost shelf to the uppermost shelf. Although a rack-and-pinion method is adopted for the elevator of this example, in another example the elevator can be a ball screw, and in a further the elevator can be a linear servo.

Figure 5:
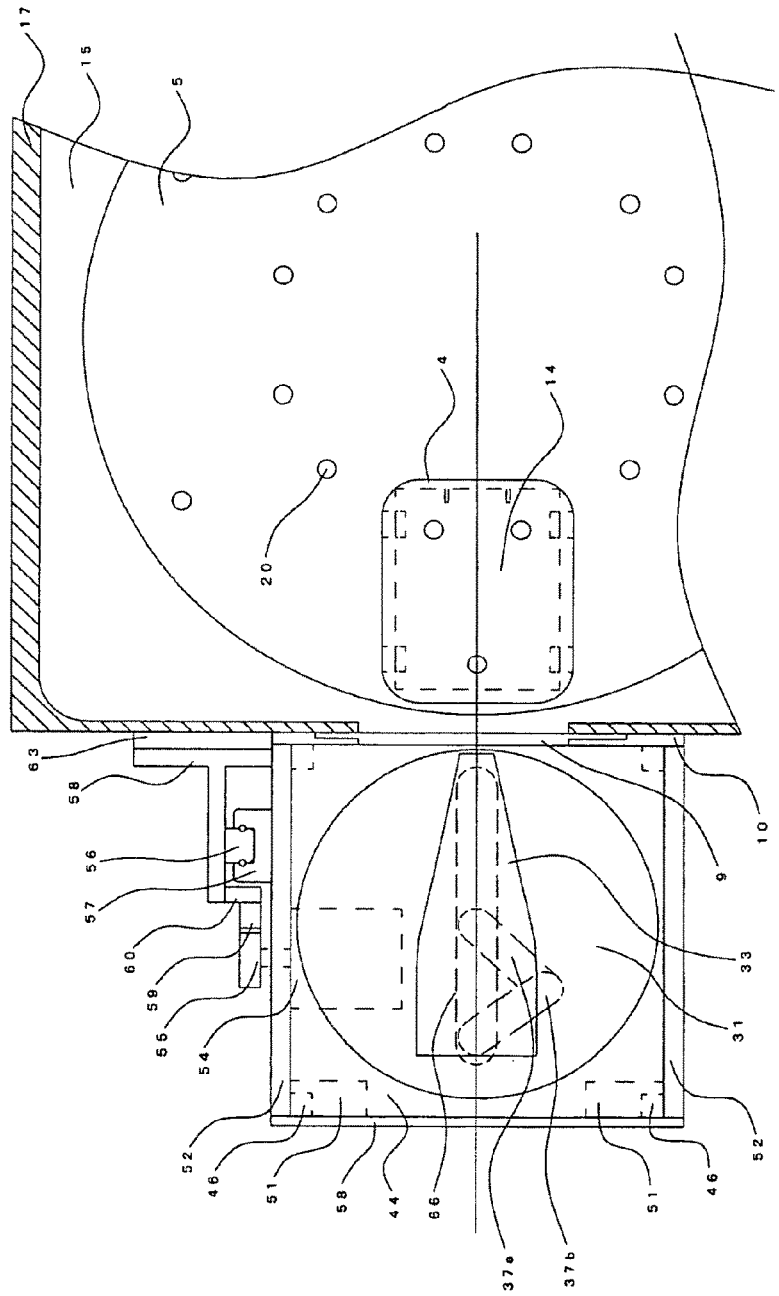
FIG. 5 is a view for explaining a physical relationship between conveyance means and a conveyed article.

As shown in FIG. 5, which illustrates the equipment viewed from the top, at a home position, the shielding plate 9 crosses at a right angle to the center line of the finger 33, and the sample table 5 is positioned so that its center of rotation intersects the center line extended of the finger 33. The finger 33 is advanced into the temperature-controlled chamber 15 through the small opening 8 by the gear motor 36, stopping at the lower tip of the sample container 14 on a sample shelf, slightly moving upwardly by rotating the rack gear 59, loading the sample container 14, and thereafter being retracted by the gear motor 36. All input-output circuits of the gear motor 36, the slewing motor 42, an elevator gear motor 54, the solenoid 61 and the sensor 49 are electrically connected to a not-illustrated control assembly. An operator can optionally set up the operation with an input such as a keyboard or the like.

Accordingly, it is possible to bring out the sample container 14 that is on the sample shelf in the temperature-controlled chamber 15, or put the sample container 14 onto the sample shelf in the temperature-controlled chamber 15 from the outside, automatically according to a moving sequence set by the operator. The conveyance mechanism 11 can be attached removably onto the box 2 by the brackets 63, 64. In carrying out dry sterilization in the temperature-controlled chamber 15, the conveyance mechanism 11 is removed to avoid the effects of heat of the dry sterilization. According to this, the risk of trouble is decreased. If the conveyor 11 is out of order, maintenance can be carried out without affecting the inside of the temperature-controlled chamber 15. Therefore, it is unnecessary to break off culturing and testing expressly, and it is possible to carry out efficient culturing and testing.

Figure 6:
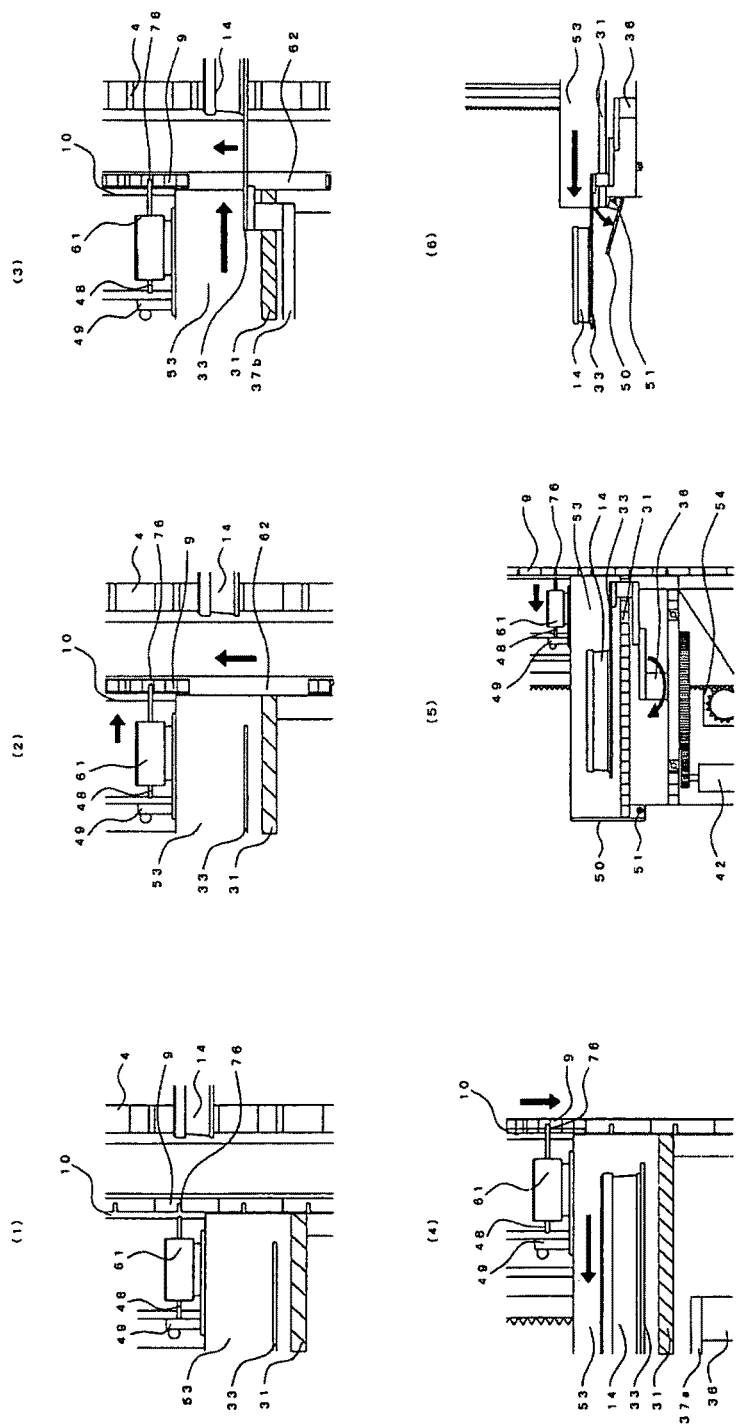
FIGS. 6(1)-6(6) are views showing the procedure for conveying a conveyed article with the conveyance mechanism.

Next, a motion for carrying a sample container 14 of the conveyance mechanism 11 will be explained with reference to FIGS. 6(1) to 6(6). Here, black arrows in the figures show the motion direction of each driving portion.

(1) As instructed by the operator, a sample shelf support 4 supporting the sample container 14 is rotatively moved to a position receive the finger 33 driven by the sample table drive mechanism 6. The engaging pin 48 of the conveyance mechanism 11 is elevated to the height of the engaging hole 76 of the shielding plates 9 corresponding to the pertinent shelf of the sample shelf support 4 by the travel mechanism 12.

(2) Positional data of each motor are sent to the control assembly at any time. When the data reach the appointed position, a signal is sent from the control assembly, so that the solenoid 61 can move the engaging pin 48 toward the shielding plates 9. The control assembly judges according to on-off signals of the sensor 49 provided behind the engaging pin 48 if the engaging pin 48 fully engages in the engaging hole 76. It is possible to confirm the position of the engaging pin 48 by setting the pin so that an optical axis of the sensor 49 can pass between the position where the rear end of the engaging pin 48 engages with the engaging hole 76 and the position insufficient for the engagement.

If the engaging pin 48 insufficiently shades, in other words, if the optical axis of the sensor 49 is kept shaded, the control assembly should be set up so that the next motion is not carried out. When the engaging pin 48 is sufficiently engaged in the engaging hole 76, the control assembly orders the travel mechanism 12 to move upward by a selected distance, so that the traveler, the shielding plate 9 engaged with the engaging pin 48, and all shielding plates above the shielding plate 9 move upward by a selected distance. According to this, upper shielding plates 65 over the shielding plate 9 that is engaged with the engaging pin 48 are moved upward within the slide frame 10 to produce a fine opening 62.

The moving amount is enough to produce the smallest opening possible to move the sample container 14 in and out, that opening being equal to the opening associated with one shelf of the sample shelf support 4 as the maximum. According to this motion, the temperature-controlled chamber 15 is opened. However, since the opening isolated with the pass box 53 in the conveyance mechanism 11 occupies only the minimum volume necessary for conveying the sample container 14, the environmental change in the chamber is held down to a minimum.

(3) When the elevator gear motor 54 finishes raising a shielding plate, the control assembly orders the gear motor 36 to advance the finger to an appointed position. Vertical positions of the finger 33 and the engaging pin 48 and the moving amount for opening the shielding plates 9 are determined according to the height of the sample container 14. When the finger 33 finishes moving forward to an appointed position below the sample container 14, the control assembly orders the travel mechanism 12 to slightly rise to lift the sample container 14.

(4) When the rise of the travel mechanism 12, driven by the elevator gear motor 54, is finished and the finger 33 holds the sample container 14, the control assembly orders the gear motor 36 to retract the finger 33 to the position where it was, and the sample container 14 is conveyed from the temperature-controlled chamber 15 to the pass box 53. When the finger 33 is retracted to the position where it was and the sample container 14 is conveyed into the pass box 53, the control assembly orders the conveyor 11 to lower the travel mechanism 12 to the position (1). According to this, the fine opening 62 is shielded and the temperature-controlled chamber 15 is a closed space again.

(5) When the conveyor 11 finishes moving the travel mechanism 12 downwardly, the control assembly orders the solenoid 61 to retract the engaging pin 48 from the engaged state to the position (1). When the sensor 49 confirms that the retraction is finished, the control assembly orders the travel mechanism 12 to go up or down the conveyance mechanism 11 to the not-illustrated predetermined position of delivery of the sample container 14. After finishing moving to the position of delivery, the control assembly orders the slewing motor 42 to rotate a rotary portion in the opposite direction by 180 degrees.

(6) After the slewing is finished, the control assembly orders the rotary source 51 of the opening/closing door 50 to open the door. After receiving a signal that opening the door is finished, the control assembly orders the gear motor 36 to advance the finger 33 to an appointed position of delivery. When the finger 33 advances to the position of delivery, the control assembly orders the elevator gear motor 54 to slightly lower the finger 33 onto a not-illustrated table and to load the sample container 14 thereon. After the delivery is finished, the control assembly orders the gear motor 36 to put the finger 33 back where it was. After the working is finished, the control assembly orders the gear motor 36 to close the opening/closing door 50. According to this, the pass box 53 again forms a closed space, and then the series of conveyance operations is complete.

According to this opening operation, the pass box 53 is open to the outside. However, since the volume of the pass box 53 is minimized as much as possible, it is possible to minimize atmosphere replacement with the outside. That is, leakage to the outside of bacteria which floats in the temperature-controlled chamber 15 can be minimized, and inflow of miscellaneous germs from the outside into the temperature-controlled chamber 15 can be also minimized.

As described above, the sample container 14 is carried out in ordered steps. In moving a sample container in, the steps from (1) to (6) can be performed in reverse.

Figure 7:
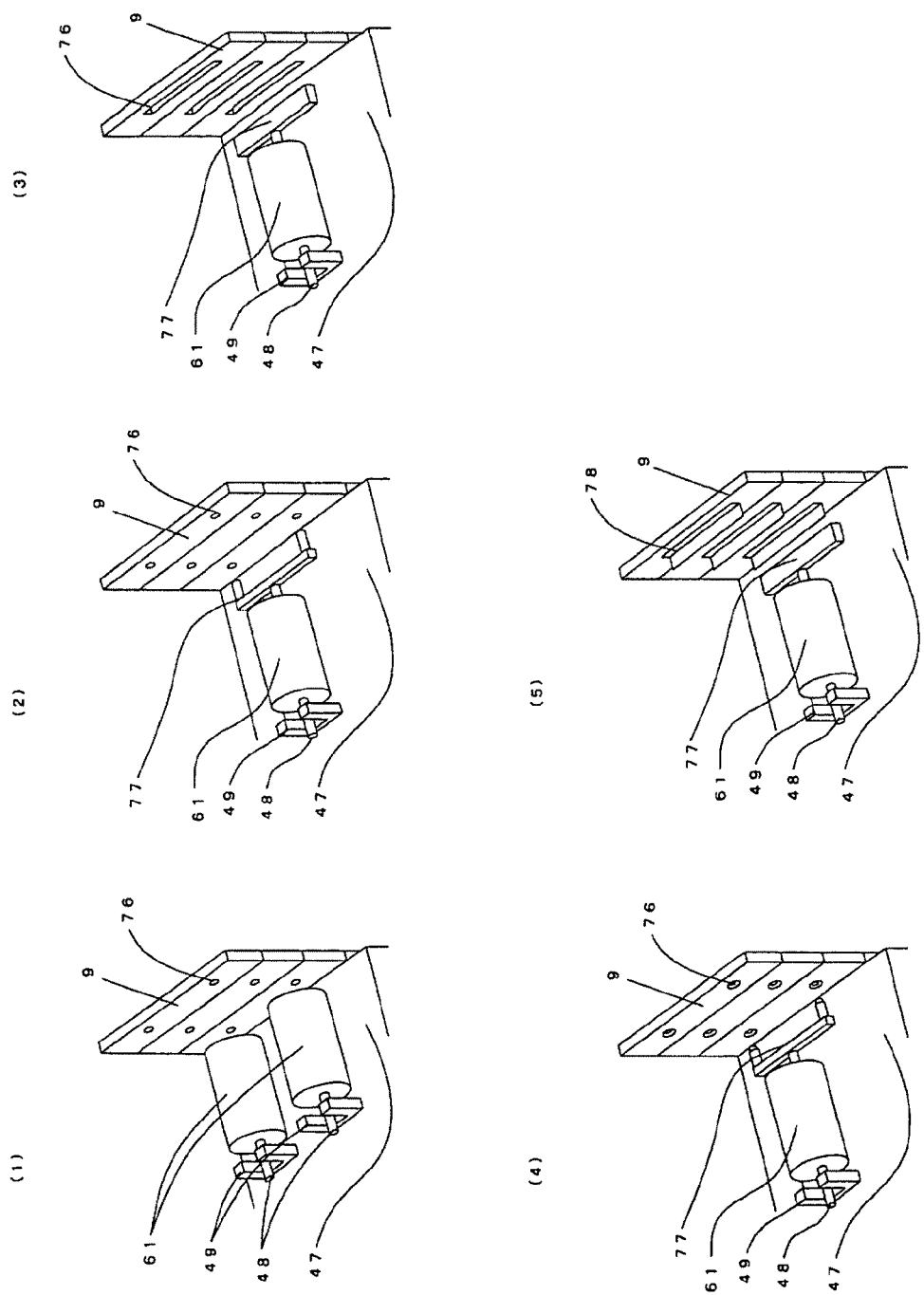
FIGS. 7(1)-7(5) are views showing various arrangements of engaging means of shielding means.

For engaging an engaging hole 76 that is provided in the shielding plates 9, five kinds of forms as shown in FIGS. 7(1) to 7(5) were carried out. In the example of FIG. 7(1), two engaging pins 49, two solenoids 61 and two sensors 49 are provided. In FIG. 7(2), the engaging pin 48 has an engaging unit 77 provided on its tip, and the solenoid 61 drives the unit. In FIG. 7(3), the engaging hole 76 and the engaging unit 77 are respectively shaped rectangularly, thereby enabling a reduction in the number of components in comparison with the case in FIG. 7(1). In FIG. 7(4), the engaging hole 76 is tapered, thereby enabling even greater assurance of engagement. In FIG. 7(5), instead of an engaging hole 76, a bracket 78 is provided, thereby enabling even more assured engagement than the arrangements of FIGS. 7(1) to 7(4). Although the position for engaging the engaging pin 49 and the engaging hole 76 of each shielding plate 9 is determined by a method for inputting instructing data to the control assembly, the position of the engaging hole 76 can be detected by installing a sensor.

Figure 8:
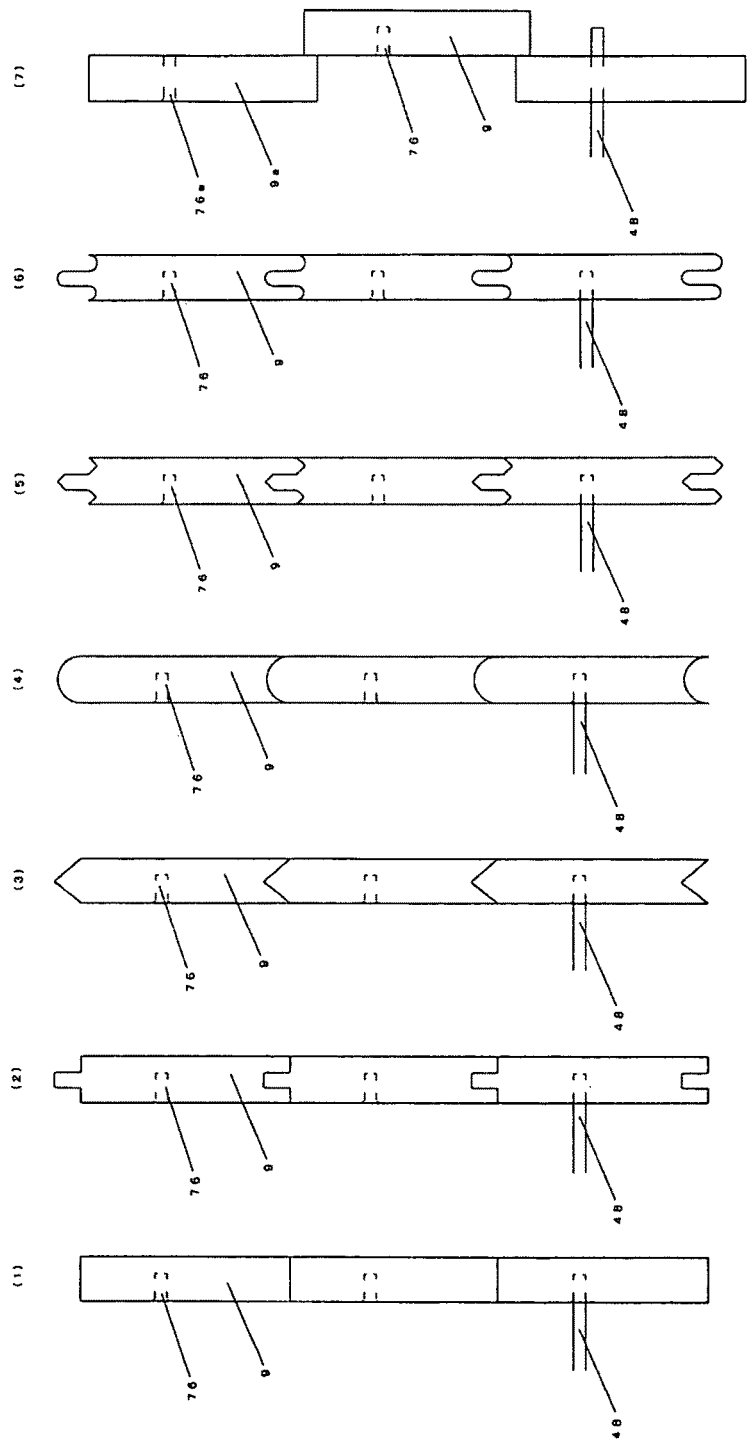
FIGS. 8(1)-8(7) are views showing various cross sections of shielding plates.

Next, the sectional form of the shielding plates will be explained with reference to FIGS. 8(1) to 8(7). FIG. 8(1) illustrates the section of the shielding plate 9 of described embodiment, whose form is the easiest to machine. However, each section in FIGS. 8(2) to 8(7) is adopted to enhance airtightness. In FIG. 8(2), making unevenness for the top and the bottom of the shielding plate 9 increases the contact area between adjacent shielding plates 9 to enhance airtightness. In FIGS. 8(3) and 8(4), repeat accuracy in opening and closing is enhanced by inclining the interfitted portions. In the case of FIG. 8(5) and FIG. 8(6), the airtightness related to FIG. 8(2) and the repeat accuracy related to FIG. 8(3) and FIG. 8(4) are compatibly enhanced, wherein the uneven portions are inclined or rounded to be easily interfitted.

In the example of FIG. 8(7), the shielding plates 9 are arranged in two rows, the plates of one row contacting the plates of the other row. The engaging hole 76a of the shielding plate 9a, which is in the row of plates adjacent to the engaging pin 48, forms a through hole. The engaging pin 48 has a stroke long enough to reach the engaging hole 76 of the shielding plate 9 which is arranged in the row of plates remote from the engaging pin 48. According to this structure, an open area equal to FIGS. 8(1) to 8(7) can be gained by moving fewer shielding plates. In addition, the shielding plates 9 are made of members that are attracted by magnetic force to enhance the airtightness of the examples of FIGS. 8(1) to 8(7). When closed, the shielding plates 9 are held against the contacting slide frame 10 with electromagnets. During opening of the small opening 8, the electricity to the electromagnets is interrupted.

Figure 14:
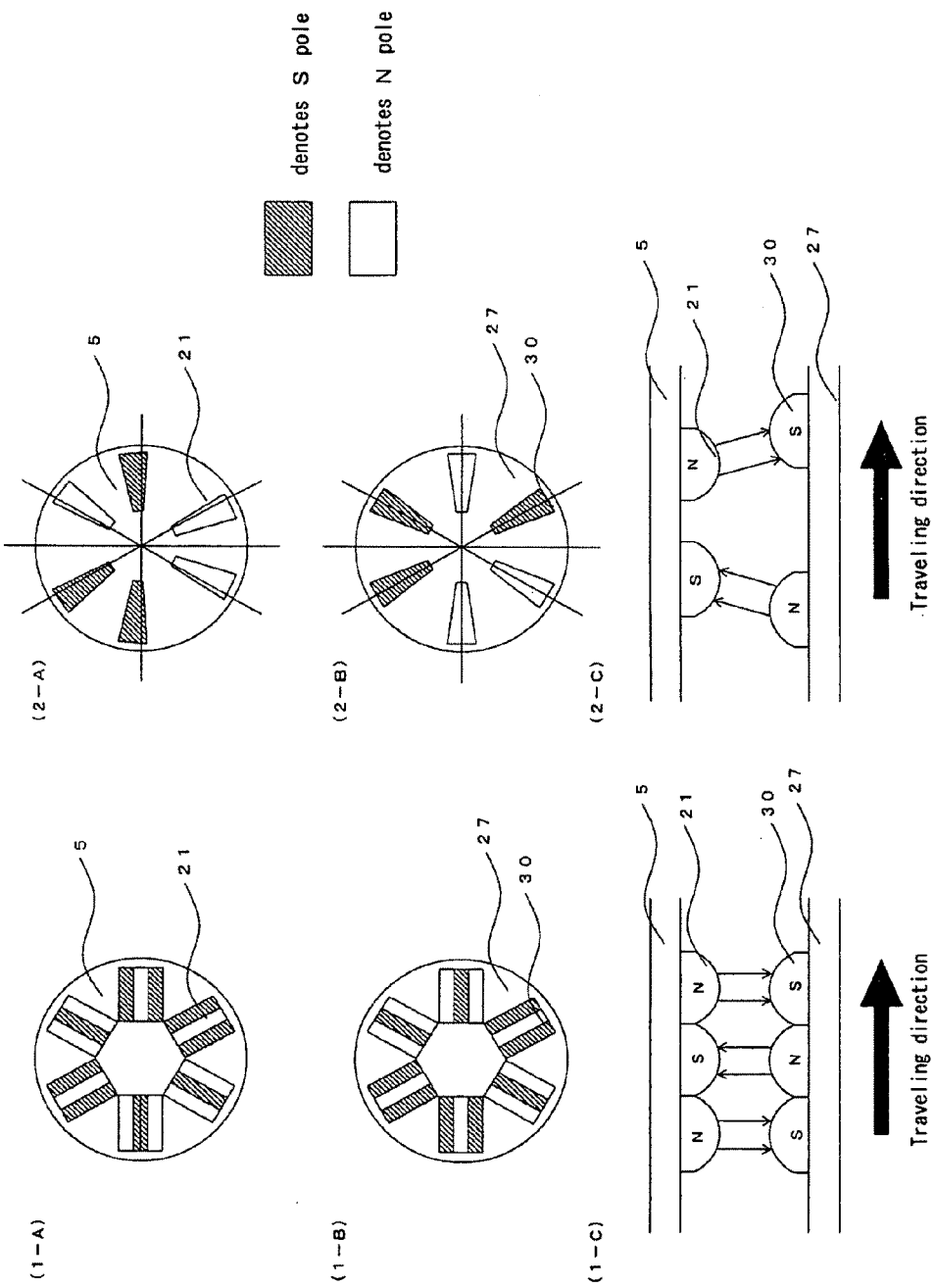
FIGS. 14(1-A)-(2-C) are views showing configurations of magnets.

The driven magnets 21 on the back of the table 5 and the driving magnets 30 arranged on the magnet housing 27 will be explained with reference to FIG. 14. Each of FIGS. 14(1-A) to 14(1-C) shows the arrangement of the magnets in this example. FIG. 14(1-A) is a view of the sample table 5 seen from the bottom, and FIG. 14(1-B) is a view of the magnet housing 27 seen from the top. FIG. 14(1-C) illustrates a vertical section of the magnets facing each other. In a stationary state, the opposite magnets pull against each other. When the magnet housing 27 is moved in a moving direction, the sample table 5 is moved by two forces which are the pulling force between the opposite magnets and the repulsion between adjacent magnets having the same magnetic polarity.

There is another example, as shown by FIGS. 14(2-A), 14(2-B) and 14(2-C). FIG. 14(2-A) is a view of the sample table 5 seen from the bottom, and FIG. 14(2-B) is a view of the magnet housing 27 seen from the top. In FIG. 14(2-B), six driving magnets 30 are arranged on the magnet housing 27 in the same configuration, and the opposite driven magnets 21 are arranged on the sample table 5 so as to be equally shifted relative to the configuration of the driving magnets 30. FIG. 14(2-C) illustrates a vertical section of the opposite magnets. Since the upper and lower magnets are arranged at positions having equal magnetic force at a fixed interval without being in alignment, the dispersion of the magnetic force decreases. Therefore, it is possible to obtain equal magnetic force with only a few magnets.

Figure 15:
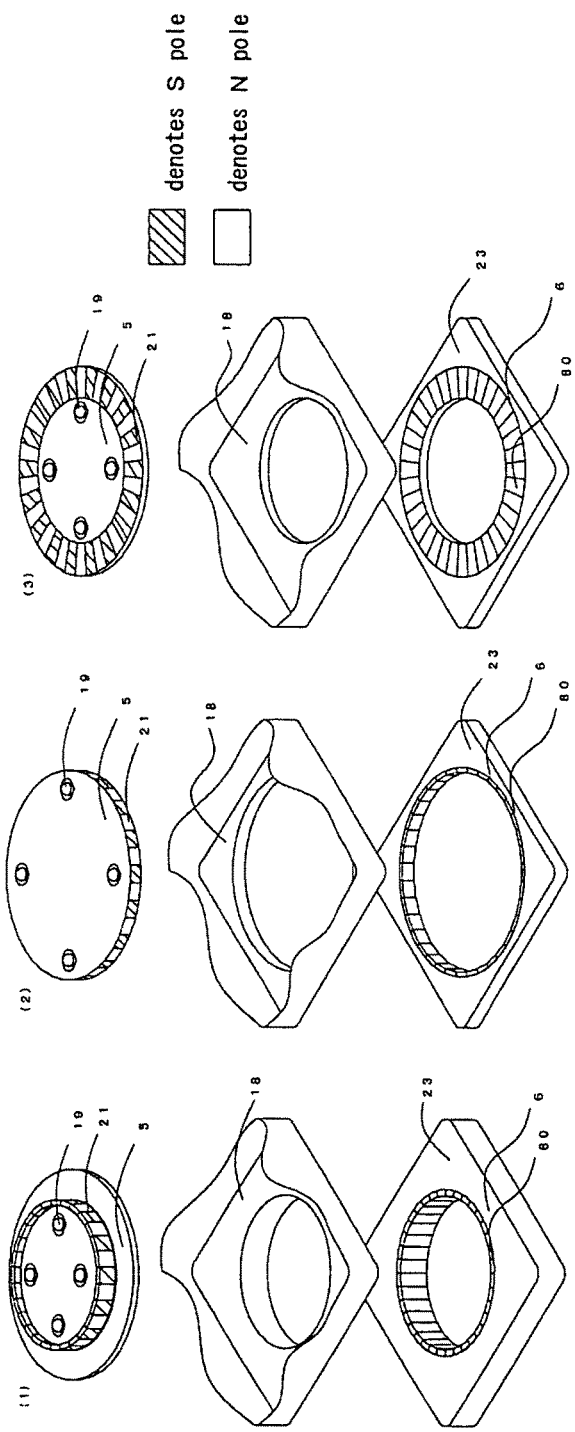
FIGS. 15(1)-(3) are views showing drive means using electromagnets.

Next, an example of a sample table 5 that is driven without the motor 24 will be explained with reference to FIG. 15. In an example of FIG. 15(1), the sample table 5 has a cylinder on the bottom, and driven magnets 21 (permanent magnets) each having different magnetic poles arranged in an alternating manner on the peripheral wall of the cylinder. In an example of FIG. 15(2), the sample table 5 is disk-like, and has the driven magnets 21 each having different magnetic poles arranged in an alternating manner on the peripheral wall of the disk. On the other hand, on the side of the sample table drive mechanism 6, a plurality of electromagnets 80 each serving as a driving magnet are arranged on the inside of the peripheral wall of the housing unit 23 so as to be opposite to the driven magnets 21. In the example of FIG. 15(3), the driven magnets 21 are arranged circumferentially on a horizontal plane. On the other hand, on the side of the sample table drive 6, the electromagnets 80 are arranged circumferentially on a horizontal plane so as to be opposite to the driven magnets 21. The sample table drive 6 has the electromagnets 80 arranged on the inside of the peripheral wall or the electromagnets 80 arranged circumferentially on a horizontal plane on the housing unit 23. In addition, the sample table drive 6 is removable attached to the temperature-controlled chamber 15 as one body by fitting the housing unit 23 to the base board 18 with the screws. In the examples of FIGS. 15(1), 15(2), 15(3), the housing unit 23 is attached removably to the bottom of the base board 18, and the inside of the temperature-controlled chamber 15 having the driven magnets 21 and the outside having the electromagnets 80 are separated by the inner wall 16. In these examples, the housing unit 23 controls the relative positional relationship of the driving magnets, which are provided on the magnet housing 27 in the example of FIG. 2.

In all examples of FIGS. 15(1), (2), (3), the electromagnet unit 80, which has magnets adjacent, or located at intervals of, the fixed number of magnets, is arranged in the driving housing unit 23 so as to respectively have opposite magnetic polarities. The sample table 5 is operated by shifting the magnetic field that is generated by switching in order the magnetic polarity of the electromagnet unit 80 through a control unit (not-illustrated) inside or outside the driving housing unit 23. The driven magnets 21 should have enough magnetic force to operate the sample table 5 even if they are not arranged over the entire circumference of the sample table 5. In addition, as with the explanation about FIG. 14(2), in switching the magnetic field of the electro-magnet unit 80, the sample table 5 is reliably moved by respectively arranging the electromagnet unit 80 of the driving side and the magnets 19 of the driven side at positions having balanced magnetic forces at equal intervals. Besides, the smoothness of the working of the sample table 5 and the accuracy of positioning are enhanced by increasing the number of electromagnets and making the sample table small and by sizing the driven magnets 21 to be equal to the electromagnets.

In these examples, a rotary magnetic field is generated as the shifting magnetic field. However, in moving the sample table 5 linearly, a linear shifting magnetic field is generated by arranging the electromagnets linearly.

Figure 16:
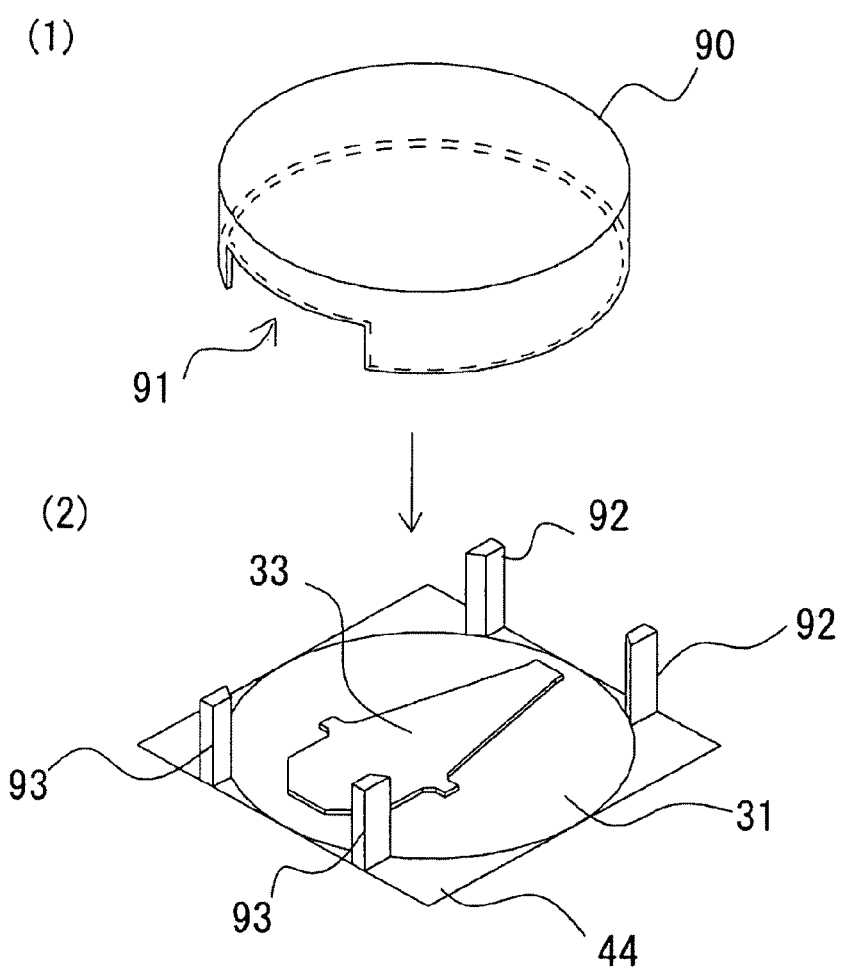
FIG. 16 is a view showing another example of a pass box 53.

FIG. 16 is a view for showing another example of the pass box 53.

FIG. 16(1) illustrates a dome 90 which is located in the inside of the pass box 53. The dome 90 forms a cylinder having a ceiling portion and a window 91. The dome 90 is mounted so as to cover a circular table 31, thereby constituting a so-called rotary door by rotating as one body with the circular table 31. Pairs of spacers 92, 93, the individual spacers in each pair being spaced from one another in accordance with the size of the window, are provided at the side of the temperature-controlled chamber 15 and on the shield shelf 44.

Figure 17:
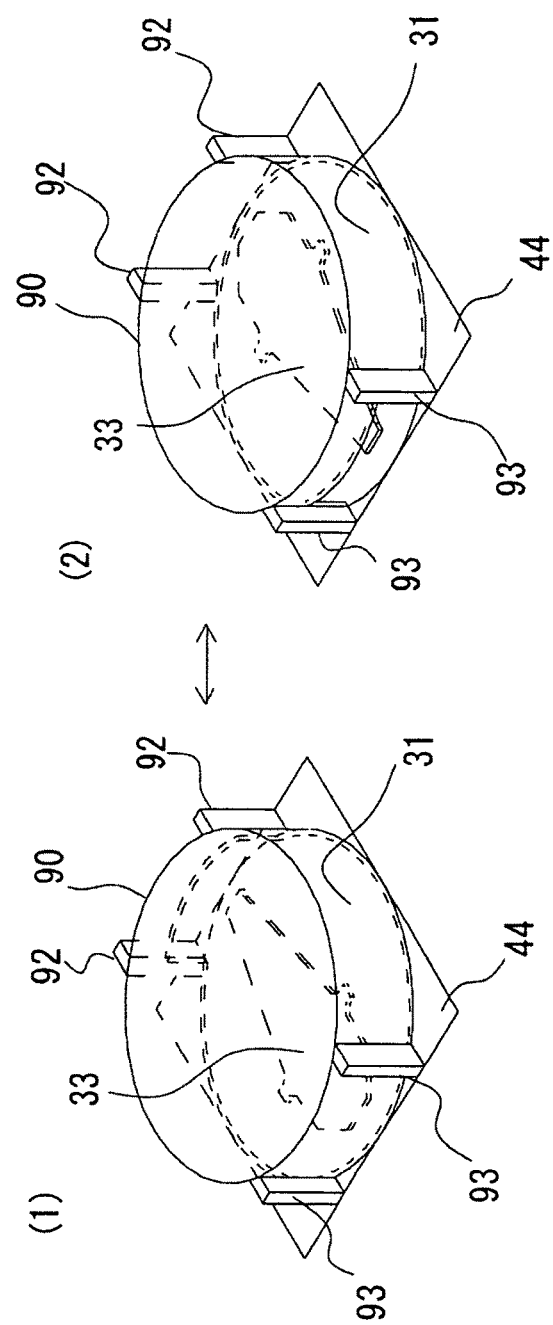
FIGS. 17(1)-(2) are views explaining the working of a dome.

As shown in FIGS. 17(1) and 17(2), when the window is positioned at the side of the temperature-controlled chamber 15 adjacent to the spacers 92, the space within the dome 90 is not in communication with the space within the pass box 53. In addition, according to the spacers 93, the effect of the atmosphere within the temperature-controlled chamber at the opposite side on the external environment can be minimized.

As explained in the above, the following embodiments can be carried out in this invention.

(1) In a constant-temperature equipment comprising a temperature-controlled chamber, means for controlling environment conditions in the temperature-controlled chamber, a sample table freely removably arranged in the temperature-controlled chamber, a sample shelf support freely removably attached on the sample table, a sample table drive mechanism for driving the sample table from the outside of the temperature-controlled chamber, a large opening portion provided on one side of the temperature-controlled chamber, a small opening portion provided on another side of the temperature-controlled chamber so that at least one sample container passes through, a conveyance mechanism for carrying in and out at least one container through the small opening portion, and a control assembly for controlling the conveyance mechanism and the sample table drive mechanism, the sample table drive mechanism being freely removable and insertable outside the temperature-controlled chamber. Here, the sample shelf support contains a plurality of containers accommodating the samples. The large opening portion is provided with a freely-opening/closing door to move in and out the sample table and/or the sample shelf support. The small opening portion is provided with a shielding plate which freely opens and closes.

(2) The conveyance mechanism can be attached removably to the external wall of the temperature-controlled chamber.

(3) The sample table has a rolling body or a low frictional member on a plane opposite to the sample table drive mechanism.

(4) The sample table drive mechanism has magnet generating means which is operated by a driving source. The sample table has driven magnets arranged at positions corresponding to the positions of the magnet generating means through members forming the temperature-controlled chamber. According to this, the driving force from the driving source is transmitted to the sample table by a non-contact coupling based on the magnetic force passing through the members forming the temperature-controlled chamber.

(5) A permanent magnet is used for the driven magnet which is provided on the sample table, and also for the magnet generating means which is provided in the sample table drive means.

(6) A permanent magnet is used for the driven magnet which is provided on the sample table, and a direct current electromagnet is used for the magnet generating means which is provided in the sample table drive means.

(7) The sample table drive mechanism, which has no movable portions, has fixed alternating current electromagnets or direct current electromagnets. The sample table has the driven magnets arranged so as to be opposite to the alternating current electromagnets or the direct current electromagnets through the members forming the inside of the temperature-controlled chamber. The driving force, which is generated by a variation of phases of the alternating current electromagnets or the direct current electromagnets, which are secured on the back side of the member forming the inside of the temperature-controlled chamber, is transmitted to the sample table by the non-contact coupling based on the magnetic force passing thorough the walls of the temperature-controlled chamber.

(8) The sample table drive mechanism is attached removably on the bottom of the temperature-controlled chamber. The sample table drive mechanism has the magnet generating means which is operated by the driving source. The sample table has the driven magnets arranged so as to be opposite to the magnet generating means through the member forming the temperature-controlled chamber. According to this, the driving force from the driving source is transmitted to the sample table by the non-contact coupling based on the magnetic force passing through the member forming the temperature-controlled chamber.

(9) The conveyance mechanism comprises a finger, an arm mechanism for moving the finger forward or rearward, slewing means for slewing the finger and the arm mechanisms, and travel means for moving the slewing means vertically or laterally.

(10) The conveyance mechanism accommodates at least the finger and the container, and has a pass box in a route for carrying the container.

(11) In addition, a shielding plate opening and closing means is provided.

(12) Plural shielding plates are arranged parallel to the travel means.

The conveyance mechanism is provided with engaging means for the shielding plates to open and close them by moving operations of the travel means.

(13) The temperature-controlled chamber has a lengthwise opening on one side plane. A plurality of shielding plates is vertically piled up inside two slide-guides which are provided on the external wall of the constant-temperature equipment outside the lengthwise opening. The conveyance mechanism lifts the opposite shielding plate and all the shielding plates above the opposite shielding plate by engaging with the opposite shielding plate. According to this, a small opening for passing at least one sample container is formed.

(14) The shielding plates are respectively opposite to the shelves of the sample shelf support at the time when the small opening is closed.

(15) The shielding plates have either an engaging hole or a bracket engaged with the engaging means of the conveyance means.

According to the above-mentioned construction, the constant-temperature equipment can rotate the sample table by having a turntable on the sample table drive means and arranging either permanent magnets or direct current electromagnets circularly around the center on the turntable.

(16) The constant-temperature equipment comprises a temperature-controlled chamber, means for controlling environment conditions in the temperature-controlled chamber, a sample table freely removably arranged in the temperature-controlled chamber, a sample shelf freely removably attached on the sample table, a sample table drive mechanism for driving the sample table from the outside of the temperature-controlled chamber, a large opening portion provided on one side of the temperature-controlled chamber, a small opening portion provided on another side of the temperature-controlled chamber so that at least one sample container passes through, a conveyance mechanism for carrying in and out at least one container through the small opening portion, and a control assembly for controlling the conveyance mechanism and the sample table drive mechanism. Here, the sample shelf support contains a plurality of containers accommodating samples. The large opening portion is provided with a freely-opening-and-closing door to move in and out the sample table and/or the sample shelf support. The small opening portion is provided with a shielding plate which freely opens and closes. In addition, the conveyance mechanism is outside the temperature-controlled chamber, being attached removably on the external wall thereof, besides having means for transmitting the driving force to the sample table by a non-contact coupling based on the magnetic force which passes through the walls of the temperature-controlled chamber separating the chamber from the outside.

(17) The temperature-controlled chamber is a chamber for accommodating the sample, being a part of constant-temperature equipment controlling the density of gas such as humidity, oxygen, nitrogen and carbon dioxide besides at least keeping a fixed indoor temperature. Especially, the constant-temperature equipment of this invention is most suitable for a culture tank which is used in biological field.

(18) The non-contact coupling based on the magnetic force can be carried out by combinations from among: permanent magnets and permanent magnets, permanent magnets and direct current electromagnets, and permanent magnets and alternating current electromagnets. In addition, a stronger magnetic force can be obtained by eliminating the dispersion of flux by respectively locating yokes on the magnets.

(19) The sample table drive mechanism has a magnet housing which rotates or moves linearly, having either permanent magnets or direct current electromagnets arranged on the magnet housing as the magnet generating means. The sample table has permanent magnets arranged as the driven magnet. Movement of the magnet housing from the driving source of the sample table drive means is turned into a following movement of the sample table by the non-contact coupling based on the magnetic force through the members forming the inside of the temperature-controlled chamber.

(20) Direct current electromagnets or alternating current electromagnets can be used for the magnet generating means arranged on the magnet housing. The strength of magnetic force can be controlled by using electromagnets, thereby easily enabling the attainment of the magnetic force most suitable for transmitting the drive force to the sample table.

(21) The sample table can be operated without using the rotary drive force from the motor. In using direct current electromagnets, the direct current electromagnets are fixed on the direct current electromagnets instead of the permanent magnets, and the magnetic poles of the direct current electromagnets are switched by the control assembly in order. In this way, the sample table can be followed by a step motion. In this case, the sample table can be precisely positioned by raising the density within the fixed interval of the direct current electromagnets.

(22) Alternating current electromagnets can be also used instead of direct current electromagnets. In this case, the drive can be made a direct drive motor type, which drives the permanent magnets located on the bottom of the sample table as a movement terminal. For all of the driving methods described herein, the sample table drive mechanism can be repaired and maintained without influencing the environment in the temperature-controlled chamber, even during testing or culturing, by removably attaching the driving structure. Since there are heat insulating materials between the inside of the temperature-controlled chamber and the installation part of the sample table drive mechanism, it is possible to avoid the structural components of the sample table drive mechanism being influenced by the atmosphere, such as a high temperature and high humidity atmosphere, in the temperature-controlled chamber during testing or culturing.

(23) The sample table is put in the temperature-controlled chamber so as to be movable. The movement method may be rotary motion or linear motion to the right and left for the small opening. Preferably, it is rotated around an axis that passes through the center of the temperature-controlled chamber.

(24) The sample table has rolling means or members having low frictional residence used as a base material provided on the bottom to surely follow the movement of the sample table drive mechanism. It is desirable that the permanent magnets located on the bottom of the sample table are separated by a constant distance from the floor of the temperature-controlled chamber, or covered with members having low frictional resistance, so as not to be worn. Similarly, in case the sample table drive mechanism has permanent magnets or direct current electromagnets, it is desirable to get rid of friction load by separating them from the bottom of the floor of the temperature-controlled chamber by a constant distance because these magnets move in themselves.

(25) The sample shelf support is so constructed that the sample containers are vertically put on a plurality of shelves. The shelves may be laterally fixed in a plurality of rows, or may be separated vertically. In the case of a disk-like sample table, the shelves are constructed so as to be integrated in a cylindrical shape along the lengthwise and the circumference or so as to be separated by every vertical line. In the latter case, the disk-like sample table has portions for carrying in and out arranged in a circle for the outside. Although the shelf supports are put on the top or the side of the positioning tool provided on the sample table, they can be fixed with screws or springs so as not to cause misregistration.

(26) Since the large opening formed on one side of the temperature-controlled chamber is rarely opened and closed while the temperature-controlled chamber is driven, it is opened and closed with a door by hand control. Here, the door may be a hinge type or a male-female type, and mounted on the side or the top. The door is preferably provided on the side of the temperature-controlled chamber, and may have a glass window fitted to observe the inside.

(27) The small opening is preferably provided just adjacent a selected shelf, not at a uniform place on the side of the temperature-controlled chamber, because it is opened at the positions of a plurality of shelves. The small opening has an opening area large enough that the conveyance mechanism can carry in and out at least one sample container. The shielding plate of the small opening may be made in a well-known shape or type. However, generally, in the case of a door having hinges at the top and the bottom, there is a risk of disturbing the atmosphere in the temperature-controlled chamber by causing an air current by opening and closing the door and by mixing the atmosphere in the temperature-controlled chamber with the atmosphere of the outside.

There is no air current problem from opening and closing when shielding plates are used, which open and close by sliding vertically or laterally, as a type of opening-and-closing door. The shielding plates are arranged between the conveyance mechanism and the external wall of the temperature-controlled chamber parallel to the travel mechanism without a gap. Here, the number of shielding plates is the same as the shelves.

(28) The sample shelf support has shelves arranged at equal intervals along its height, and the shielding plates may correspond to the shelves. For example, in putting a sample container having the size of two shelves on a sample shelf, a partition between the shelves is removed. The size of the shielding plate may be equal to the height of each shelf of the sample shelf or may not. However, when it is recognized that a big container is put on beforehand, the pass box or the dome must be large enough to accommodate the big container.

(29) The conveyance mechanism comprises a finger, an arm mechanism for advancing and retracting the finger, and a travel mechanism for laterally or vertically moving the finger and the arm mechanism. The conveyance mechanism has a pass box having the minimum capacity necessary for accommodating the sample container, being constructed so as not to have a harmful influence on the internal environment while carrying the sample container in and out. Although it is preferable that there is no opening between the pass box and the shielding plates, means for improving the airtightness, such as a packing etc. also can be provided.

(30) The conveyance mechanism is attached removably on the external wall adjacent to the small opening of the temperature-controlled chamber, thereby enabling repair and maintainenance without affecting the environment in the temperature-controlled chamber, even during testing or cultivating. Since the conveyance mechanism is mounted on the outside, the components of the conveyance mechanism are not affected by the atmosphere of high temperature and high humidity in the temperature-controlled chamber.

(31) The conveyance mechanism engages with the shielding plates, opening-and-closing the shielding plates from the outside of the temperature-controlled chamber without a drive mechanism that is only for opening and closing them. That is, the conveyance mechanism and the shielding plates are integrally interlocked by the engaging means, enabling the shielding plates to be opened and closed by the travel of a part of the conveyance mechanism, without a drive mechanism that is exclusively for opening and closing. According to this, the conveyance mechanism has few components and a simple structure, thereby enabling a reduction in cost and improvement in reliability. As for the engaging means, mechanical connection due to bar members or connection due to magnetic force are contemplated.

(32) The shielding plates can be lined up by the slide-guides movably in the vertical direction or the lateral direction. The shielding plates can improve the tightness between the adjoining portions by forming the sections of the adjoining portions in a curb or a plurality of straight lines which can be interfitted.

(33) To improve the airtightness between the shielding plates and the external wall of the constant-temperature equipment, the shielding plates are made of members which are attracted by magnetic force or provided with a member that is attracted by magnetic force, and a magnet is provided at a position where it causes the shielding plate to contact the external wall of the temperature-controlled chamber. According to this, the shielding plate and the external wall of the temperature-controlled chamber are held together by the magnetic force, thereby improving the airtightness.

(34) A pulse motor, such as a stepping motor or a servomotor, is preferably used as the motor for the conveyance mechanism and as the motor for the sample table drive mechanism. A control device is provided to automatically control these motors and to control the environmental conditions in the temperature-controlled chamber.

(35) It is preferable that there are no projections such as a rotating shaft and a fixed shelf in the temperature-controlled chamber of the constant-temperature equipment. Further, it is preferable that the inside of the temperature-controlled chamber is smooth so as to be easily cleaned. However, it is possible to form holes for supplying or discharging gases such as humid air for controlling the environmental conditions, including oxygen, nitrogen and carbon dioxide, and to provide sensors for the temperature, the humidity and the concentration of various gases. In this case, the inside may be constructed so as not to be influenced by the outside environment by maintaining it at a positive pressure.

(36) The well-known technology, such as a sump for humidification and a mechanism for dew-condensation, may be used in the temperature-controlled chamber. The temperature-controlled chamber can accommodate a pool of demineralized water, because the floor is flat without mechanical components. In addition, the humidity during testing and culturing can be maintained by forming the sump out of concavities composed of a smooth curved plane or by placing vats at four corners of the floor of the temperature-controlled chamber.

(37) Although the sample table is moved in a non-contact manner by the magnetic coupling in the above-mentioned examples, it can be moved by mechanical constituents such as a shaft which passes through from a motor installed on the outside of the temperature-controlled chamber into the temperature-controlled chamber, as is shown in Japanese Patent Laid Open Publication No. 2001-172 and Japanese Patent Laid Open Publication No. 2005-500522.

(39) As a detachable piece, a magnetic coupling for moving the shielding plate with electromagnets can be used instead of a mechanical coupling such as the engaging pin.

According to these embodiments, the following effects can be obtained.

As shown in FIG. 2, because all of the electrical and mechanical structures, such as the sample shelf support 4, the sample table 5, the sample table drive mechanism 6, the conveyance mechanism 11 and the travel mechanism 12 are removed from the temperature-controlled chamber 15, dry sterilization at a high temperature, which was difficult with the conventional automatic incubators, can be carried out with all of the remaining structures in the temperature-controlled chamber 15. In this case, the components do not break down at the high temperature at the time of the dry sterilization, because the electrical and mechanical structures have been removed.

Since the temperature-controlled chamber has no irregularities due to the electrical and mechanical structures, it is possible to easily wipe the chamber before and after sterilization and carry out highly reliable sterilization. Therefore, it is possible to carry out highly reliable culturing and testing. Since the sample shelf support 4 and the sample table 5 can be easily removed from the temperature-controlled chamber 15, they can be individually sterilized and washed in sterilized liquid.

Since the temperature-controlled chamber 15 has no electrical and mechanical structures for the driving portion and has the insulating materials 22 put along the portion connected to the sample table drive 6, the driving portion is not affected by the atmosphere of high temperature and humidity. Therefore, the driving portion hardly breaks down, thereby enabling the avoidance of suspensions or interruptions of the culturing and testing caused by such breakdowns.

If the electrical and mechanical structures should break down during the culturing and testing, the sample table drive mechanism 6 and the conveyance mechanism 11 can be removed and repaired, because the sample table drive mechanism 6, the conveyance means 11 and the temperature-controlled chamber 15 are completely separate from one another. Therefore, it is possible to avoid suspensions of the culturing and testing. In addition, a good culture environment can be maintained by providing means for maintaining the humidity during the culturing and testing.

Since the temperature-controlled chamber 15 has a planar bottom without mechanical components, it is possible to pool pure water therein to maintain humidity during the culturing and testing.

Since the conveyor 11 has the pass box having the minimum capacity necessary for carrying the container, the internal environment, which is kept at constant temperature and humidity, is not affected by carrying a container in and out. Therefore, it is possible to maintain a stable culturing and testing environment.

Since the slide type is adopted for opening and closing the shielding plates and the shielding plates except those at the required openings are always closed, unnecessary airflow is not generated in the temperature-controlled chamber at the time of the opening and closing. Therefore, it is possible to maintain a stable culturing and testing environment.

The invention claimed is:

1. Constant-temperature equipment comprising:
   a temperature-controlled chamber having a sample shelf support and an opening portion, said sample shelf support being provided inside the chamber and having a plurality of shelves, and said opening portion being openable to the outside at positions corresponding to each shelf of the sample shelf support;
   a slide frame extending along a side edge of the opening portion;
   a plurality of shielding plates for closing the opening portion, said shielding plates being guided by the slide frame for sliding along the slide frame, each of said shielding plates closing or opening an interval with an adjoining shielding plate while being guided by the slide frame and while moving all of the shielding plates that are positioned vertically above said shielding plate; and a conveyance mechanism, the conveyance mechanism having a portion selectively engageable with the shielding plates, the conveyance mechanism sliding the shielding plates along the slide frame.

2. A constant-temperature equipment according to claim 1, further comprising a pass box having a finger, an arm mechanism for advancing and retracting the finger, and a slewing mechanism for slewing the finger and the arm mechanism, wherein the selectively engageable portion is mounted on the outside of the pass box.

3. A constant-temperature equipment according to claim 2, further having a dome in the pass box, said dome having an opening at one side and rotating as one body with the slewing mechanism, wherein the finger and the arm mechanism are located in the dome.

4. A constant-temperature equipment according to claim 2, wherein the opening portion forms a lengthwise opening, the slide frame guides the shielding plates vertically, the selectively engageable portion is engageable with any of the shielding plates, and upward movement of the conveyance mechanism connects a space within the pass box and a space within the sample shelf support by lifting an engaged shielding plate and any shielding plates above the engaged shielding plate.

5. A constant-temperature equipment according to claim 1, wherein the shielding plates are in alignment with spaces between the shelves of the sample shelf support.

6. A constant-temperature equipment according to claim 1, wherein the shielding plates have engaging holes or brackets, and the selectively engageable portion is engageable with one of the engaging holes or brackets.

7. A constant-temperature equipment according to claim 1, wherein a bracket for fitting and removing the conveyance mechanism is provided on the temperature-controlled chamber.

\* \* \* \* \*